(12) United States Patent
Harris et al.

(10) Patent No.: US 10,548,590 B2
(45) Date of Patent: *Feb. 4, 2020

(54) SYSTEM AND METHOD FOR ALL-INSIDE SUTURE FIXATION FOR IMPLANT ATTACHMENT AND SOFT TISSUE REPAIR

(71) Applicant: Ivy Sports Medicine, LLC, Montvale, NJ (US)

(72) Inventors: Stephen Vaughan Harris, Redwood City, CA (US); Nadine Beverly Nelson, Belmont, CA (US)

(73) Assignee: Ivy Sports Medicine, LLC, Montvale, NJ (US)

( * ) Notice: Subject to any disclaimer, the term of this patent is extended or adjusted under 35 U.S.C. 154(b) by 416 days.

This patent is subject to a terminal disclaimer.

(21) Appl. No.: 15/226,521

(22) Filed: Aug. 2, 2016

(65) Prior Publication Data

US 2017/0027557 A1 Feb. 2, 2017

Related U.S. Application Data

(63) Continuation of application No. 13/410,501, filed on Mar. 2, 2012, now Pat. No. 9,402,616, which is a
(Continued)

(51) Int. Cl.
*A61B 17/04* (2006.01)
*A61B 17/06* (2006.01)

(52) U.S. Cl.
CPC ...... *A61B 17/0469* (2013.01); *A61B 17/0401* (2013.01); *A61B 17/0467* (2013.01);
(Continued)

(58) Field of Classification Search
CPC ............ A61B 17/0401; A61B 17/0467; A61B 17/0469; A61B 2017/0417;
(Continued)

(56) References Cited

U.S. PATENT DOCUMENTS 2,269,963 A * 1/1942 Wappler ............ A61M 37/0069
604/61
3,103,666 A 9/1963 Bone
(Continued)

FOREIGN PATENT DOCUMENTS

DE 102010060899 A1 5/2012
EP 0129442 A1 12/1984
(Continued)

OTHER PUBLICATIONS

Supplementary European Search Report for Application No. 16173415.7 dated Jan. 16, 2017.
(Continued)

*Primary Examiner* — Dianne Dornbusch
(74) *Attorney, Agent, or Firm* — Lerner, David, Littenberg, Krumholz & Mentlik, LLP

(57) ABSTRACT

A system for repairing a meniscus includes a suture that includes a first anchor, a second anchor, and a flexible portion connecting the first anchor and the second anchor. The flexible portion includes a self-locking slide knot between the first anchor and the second anchor. The system also includes a needle having a longitudinal extending bore and an open end. The bore is configured to receive the first anchor and the second anchor. The system further includes a body portion operatively connected to the needle at a distal end of the body portion. The body portion has a lumen. The system also includes a pusher configured to rotate and slide within the lumen of the body portion and the longitudinal extending bore of the needle. The pusher has first and second stop surfaces, each of which is constructed and arranged to engage a proximal end of the body portion.

15 Claims, 20 Drawing Sheets

Related U.S. Application Data continuation of application No. 11/501,235, filed on Aug. 9, 2006, now Pat. No. 8,128,640, which is a continuation-in-part of application No. 11/348,467, filed on Feb. 7, 2006, now Pat. No. 8,808,309.

(60) Provisional application No. 60/650,131, filed on Feb. 7, 2005.

(52) U.S. Cl.
CPC .......... *A61B 2017/0417* (2013.01); *A61B 2017/0458* (2013.01); *A61B 2017/0464* (2013.01); *A61B 2017/0474* (2013.01); *A61B 2017/0475* (2013.01); *A61B 2017/0496* (2013.01); *A61B 2017/06052* (2013.01)

(58) Field of Classification Search
CPC .... A61B 2017/0458; A61B 2017/0403; A61B 2017/0404; A61B 2017/0406; A61B 2017/0408; A61B 2017/0409; A61B 2017/0414; A61B 2017/0419; A61B 2017/0445; A61B 2017/0464
See application file for complete search history.

(56) References Cited

U.S. PATENT DOCUMENTS

| | | | | |
|---|---|---|---|---|
| 3,110,310 A | * | 11/1963 | Cislak | A61M 5/31581 604/209 |
| 3,399,432 A | | 9/1968 | Merser | |
| 3,527,223 A | | 9/1970 | Shein | |
| 3,845,772 A | | 11/1974 | Smith | |
| 3,875,648 A | | 4/1975 | Bone | |
| 3,990,619 A | * | 11/1976 | Russell | B65C 7/005 227/67 |
| 4,178,810 A | * | 12/1979 | Takahashi | A61B 10/06 403/166 |
| 4,235,238 A | | 11/1980 | Ogiu et al. | |
| 4,339,058 A | * | 7/1982 | Wendt | G01F 11/026 222/309 |
| 4,367,738 A | * | 1/1983 | Legendre | A61M 5/5013 604/110 |
| 4,444,335 A | * | 4/1984 | Wood | A61M 3/00 222/309 |
| 4,466,426 A | * | 8/1984 | Blackman | A61M 5/3158 600/5 |
| 4,491,132 A | * | 1/1985 | Aikins | A61B 17/32001 30/162 |
| 4,493,323 A | | 1/1985 | Albright et al. | |
| 4,614,187 A | * | 9/1986 | Mulhollan | A61B 17/0469 606/144 |
| 4,642,102 A | * | 2/1987 | Ohmori | A61M 5/31555 604/210 |
| 4,669,473 A | | 6/1987 | Richards et al. | |
| 4,705,040 A | | 11/1987 | Mueller et al. | |
| 4,741,330 A | | 5/1988 | Hayhurst | |
| 4,826,483 A | * | 5/1989 | Molnar, IV | A61M 5/5013 604/110 |
| 4,836,205 A | | 6/1989 | Barrett | |
| 4,840,616 A | * | 6/1989 | Banks | A61M 5/5013 604/110 |
| 4,906,231 A | * | 3/1990 | Young | A61M 5/5013 604/110 |
| 4,950,163 A | * | 8/1990 | Zimble | A61C 19/06 433/215 |
| 4,978,339 A | * | 12/1990 | Labouze | A61M 5/5013 604/110 |
| 4,994,074 A | | 2/1991 | Bezwada et al. | |
| 5,021,047 A | * | 6/1991 | Movern | A61M 5/5013 604/110 |
| 5,085,661 A | | 2/1992 | Moss | |
| 5,109,780 A | * | 5/1992 | Slouf | D05C 15/06 112/169 |
| 5,149,329 A | * | 9/1992 | Richardson | A61B 17/04 128/898 |
| 5,176,691 A | | 1/1993 | Pierce | |
| 5,222,942 A | * | 6/1993 | Bader | A61M 5/5013 604/110 |
| 5,250,030 A | * | 10/1993 | Corsich | A61M 5/5013 604/110 |
| 5,312,422 A | | 5/1994 | Trott | |
| 5,328,077 A | * | 7/1994 | Lou | A61B 17/00234 227/107 |
| 5,380,295 A | * | 1/1995 | Vacca | A61M 5/315 604/187 |
| 5,380,334 A | | 1/1995 | Torrie et al. | |
| 5,391,182 A | | 2/1995 | Chin | |
| 5,405,352 A | | 4/1995 | Weston | |
| 5,417,691 A | | 5/1995 | Hayhurst | |
| 5,437,680 A | | 8/1995 | Yoon | |
| 5,443,475 A | | 8/1995 | Auerbach et al. | |
| 5,467,786 A | | 11/1995 | Allen et al. | |
| 5,470,337 A | * | 11/1995 | Moss | A61B 17/0401 606/139 |
| 5,507,754 A | * | 4/1996 | Green | A61B 17/0401 112/169 |
| 5,549,631 A | * | 8/1996 | Bonutti | A61B 17/0401 606/232 |
| 5,562,623 A | * | 10/1996 | Shonfeld | A61M 5/5013 604/110 |
| 5,562,684 A | | 10/1996 | Kammerer | |
| 5,562,689 A | | 10/1996 | Green et al. | |
| 5,569,305 A | | 10/1996 | Bonutti | |
| 5,601,557 A | | 2/1997 | Hayhurst | |
| 5,601,558 A | | 2/1997 | Torrie et al. | |
| 5,601,571 A | | 2/1997 | Moss | |
| 5,601,576 A | | 2/1997 | Garrison | |
| 5,626,614 A | | 5/1997 | Hart | |
| 5,649,947 A | | 7/1997 | Auerbach et al. | |
| 5,667,513 A | | 9/1997 | Torrie et al. | |
| 5,702,462 A | | 12/1997 | Oberlander | |
| 5,718,717 A | | 2/1998 | Bonutti | |
| 5,759,189 A | | 6/1998 | Ferragamo et al. | |
| 5,801,848 A | | 9/1998 | Kafri | |
| 5,810,848 A | * | 9/1998 | Hayhurst | A61B 17/04 606/139 |
| 5,871,504 A | * | 2/1999 | Eaton | A61F 2/0805 606/232 |
| 5,895,395 A | | 4/1999 | Yeung | |
| 5,928,252 A | | 7/1999 | Steadman et al. | |
| 5,941,439 A | | 8/1999 | Kammerer et al. | |
| 5,948,002 A | * | 9/1999 | Bonutti | A61B 17/0401 606/104 |
| 5,976,127 A | | 11/1999 | Lax | |
| 5,980,559 A | | 11/1999 | Bonutti | |
| 6,039,753 A | | 3/2000 | Meislin | |
| 6,047,826 A | | 4/2000 | Kalinski et al. | |
| 6,056,760 A | | 5/2000 | Koike et al. | |
| 6,066,146 A | * | 5/2000 | Carroll | A61B 17/0401 606/144 |
| 6,071,292 A | | 6/2000 | Makower et al. | |
| 6,156,044 A | | 12/2000 | Kammerer et al. | |
| 6,162,192 A | * | 12/2000 | Cragg | A61B 17/0057 604/15 |
| 6,206,895 B1 | | 3/2001 | Levinson | |
| 6,283,941 B1 | * | 9/2001 | Schoenfeld | A61M 5/5013 604/110 |
| 6,287,317 B1 | | 9/2001 | Makower et al. | |
| 6,293,961 B2 | | 9/2001 | Schwartz et al. | |
| 6,306,156 B1 | | 10/2001 | Clark | |
| 6,306,159 B1 | | 10/2001 | Schwartz et al. | |
| 6,315,753 B1 | * | 11/2001 | Cragg | A61B 17/0057 604/15 |
| 6,319,263 B1 | | 11/2001 | Levinson | |
| 6,319,271 B1 | | 11/2001 | Schwartz et al. | |
| 6,432,123 B2 | | 8/2002 | Schwartz et al. | |
| 6,488,691 B1 | * | 12/2002 | Carroll | A61B 17/0401 606/148 |
| 6,491,707 B2 | | 12/2002 | Makower et al. | |
| 6,500,195 B2 | | 12/2002 | Bonutti | |

(56) References Cited

U.S. PATENT DOCUMENTS

| | | | |
|---|---|---|---|
| 6,527,734 B2 * | 3/2003 | Cragg | A61B 17/0057 604/15 |
| 6,533,756 B2 * | 3/2003 | Schoenfeld | A61M 5/5013 604/110 |
| 6,554,845 B1 * | 4/2003 | Fleenor | A61B 17/0469 606/139 |
| 6,572,635 B1 | 6/2003 | Bonutti | |
| 6,592,609 B1 | 7/2003 | Bonutti | |
| 6,610,026 B2 * | 8/2003 | Cragg | A61B 17/0057 604/15 |
| 6,626,916 B1 | 9/2003 | Yeung et al. | |
| 6,635,073 B2 | 10/2003 | Bonutti | |
| 6,656,182 B1 | 12/2003 | Hayhurst | |
| 6,730,112 B2 | 5/2004 | Levinson | |
| 6,884,249 B2 | 4/2005 | May et al. | |
| 6,932,826 B2 | 8/2005 | Chan | |
| 6,955,683 B2 | 10/2005 | Bonutti | |
| 6,972,027 B2 * | 12/2005 | Fallin | A61B 17/0401 606/139 |
| 6,997,933 B2 | 2/2006 | Bittar | |
| 7,004,959 B2 | 2/2006 | Bonutti | |
| 7,004,970 B2 | 2/2006 | Cauthen, III et al. | |
| 7,025,756 B2 | 4/2006 | Frazier et al. | |
| 7,033,380 B2 | 4/2006 | Schwartz et al. | |
| 7,048,710 B1 * | 5/2006 | Cragg | A61B 17/0057 604/15 |
| 7,056,325 B1 | 6/2006 | Makower et al. | |
| 7,066,944 B2 | 6/2006 | Laufer et al. | |
| 7,087,073 B2 * | 8/2006 | Bonutti | A61B 17/0401 606/215 |
| 7,108,700 B2 | 9/2006 | Chan | |
| 7,118,583 B2 | 10/2006 | O'Quinn et al. | |
| 7,150,750 B2 | 12/2006 | Damarati | |
| 7,153,312 B1 * | 12/2006 | Torrie | A61B 17/0401 606/144 |
| 7,192,431 B2 | 3/2007 | Hangody et al. | |
| 7,318,833 B2 | 1/2008 | Chanduszko | |
| 7,320,701 B2 * | 1/2008 | Haut | A61B 17/0401 606/232 |
| 7,347,863 B2 | 3/2008 | Rothe et al. | |
| 7,361,180 B2 | 4/2008 | Saadat et al. | |
| 7,390,329 B2 | 6/2008 | Westra et al. | |
| 7,390,332 B2 * | 6/2008 | Selvitelli | A61B 17/0401 606/144 |
| 7,594,922 B1 | 9/2009 | Goble et al. | |
| 7,601,165 B2 | 10/2009 | Stone | |
| 7,601,659 B2 | 10/2009 | Bomberger et al. | |
| 7,608,092 B1 | 10/2009 | Schaffhausen | |
| 7,608,098 B1 | 10/2009 | Stone et al. | |
| 7,611,479 B2 * | 11/2009 | Cragg | A61B 17/0057 604/11 |
| 7,621,925 B2 | 11/2009 | Saadat et al. | |
| 7,645,286 B2 | 1/2010 | Catanese, III et al. | |
| 7,651,509 B2 * | 1/2010 | Bojarski | A61B 17/0401 606/139 |
| 7,658,751 B2 | 2/2010 | Stone et al. | |
| 7,736,374 B2 | 6/2010 | Vaughan et al. | |
| 7,749,250 B2 | 7/2010 | Stone et al. | |
| 7,846,181 B2 | 12/2010 | Schwartz et al. | |
| 7,857,830 B2 | 12/2010 | Stone et al. | |
| 7,887,551 B2 | 2/2011 | Bojarski et al. | |
| 7,905,903 B2 | 3/2011 | Stone et al. | |
| 7,905,904 B2 | 3/2011 | Stone et al. | |
| 7,909,851 B2 | 3/2011 | Stone et al. | |
| 7,914,539 B2 | 3/2011 | Stone et al. | |
| 7,959,650 B2 | 6/2011 | Kaiser et al. | |
| 7,993,405 B2 | 8/2011 | Cauthen, III et al. | |
| 8,034,090 B2 | 10/2011 | Stone et al. | |
| 8,057,511 B2 | 11/2011 | Flores et al. | |
| RE43,143 E | 1/2012 | Hayhurst | |
| 8,088,130 B2 | 1/2012 | Kaiser et al. | |
| 8,118,836 B2 | 2/2012 | Denham et al. | |
| 8,128,640 B2 | 3/2012 | Harris et al. | |
| 8,137,382 B2 | 3/2012 | Denham et al. | |
| 8,202,282 B2 | 6/2012 | Schmieding et al. | |
| 8,216,252 B2 | 7/2012 | Vaughan et al. | |
| 8,216,253 B2 | 7/2012 | Saadat et al. | |
| 8,231,654 B2 | 7/2012 | Kaiser et al. | |
| 8,236,009 B2 | 8/2012 | Saadat et al. | |
| 8,241,305 B2 | 8/2012 | Stone | |
| 8,251,998 B2 | 8/2012 | Hoeppner et al. | |
| 8,257,394 B2 | 9/2012 | Saadat et al. | |
| 8,273,106 B2 | 9/2012 | Stone et al. | |
| 8,292,921 B2 | 10/2012 | Stone et al. | |
| 8,298,262 B2 | 10/2012 | Stone et al. | |
| 8,303,604 B2 | 11/2012 | Stone et al. | |
| 8,308,765 B2 | 11/2012 | Saadat et al. | |
| 8,317,825 B2 | 11/2012 | Stone | |
| 8,323,315 B2 | 12/2012 | Schwartz et al. | |
| 8,337,525 B2 | 12/2012 | Stone et al. | |
| 8,343,227 B2 | 1/2013 | Metzger et al. | |
| 8,361,113 B2 | 1/2013 | Stone et al. | |
| 8,366,744 B2 | 2/2013 | Bojarski et al. | |
| 8,409,253 B2 | 4/2013 | Stone et al. | |
| 8,444,657 B2 | 5/2013 | Saadat et al. | |
| 8,460,319 B2 | 6/2013 | Wales et al. | |
| 8,500,818 B2 | 8/2013 | Metzger et al. | |
| 8,506,597 B2 | 8/2013 | Kaiser et al. | |
| 8,512,374 B2 | 8/2013 | Schwartz et al. | |
| 8,512,375 B2 | 8/2013 | Torrie et al. | |
| 8,551,140 B2 | 10/2013 | Denham et al. | |
| 8,562,645 B2 | 10/2013 | Stone et al. | |
| 8,562,647 B2 | 10/2013 | Kaiser et al. | |
| 8,574,235 B2 | 11/2013 | Stone | |
| 8,597,327 B2 | 12/2013 | Stone et al. | |
| 8,623,051 B2 | 1/2014 | Bojarski et al. | |
| 8,632,569 B2 | 1/2014 | Stone et al. | |
| 8,652,153 B2 | 2/2014 | Brady et al. | |
| 8,696,704 B2 | 4/2014 | Selvitelli et al. | |
| 8,790,369 B2 | 7/2014 | Orphanos et al. | |
| 8,808,309 B2 | 8/2014 | Nelson et al. | |
| 8,814,902 B2 | 8/2014 | Bonutti | |
| 8,814,903 B2 | 8/2014 | Sengun et al. | |
| 8,814,904 B2 | 8/2014 | Bennett | |
| 8,828,027 B2 | 9/2014 | Vaughan et al. | |
| 8,828,052 B2 | 9/2014 | Caborn et al. | |
| 8,828,054 B2 | 9/2014 | Caborn et al. | |
| 8,834,524 B2 | 9/2014 | Torrie et al. | |
| 8,876,842 B2 | 11/2014 | Marshall et al. | |
| 8,926,634 B2 | 1/2015 | Rothe et al. | |
| 8,961,538 B2 | 2/2015 | Koogle, Jr. et al. | |
| 9,084,597 B2 | 7/2015 | Arai et al. | |
| 9,173,645 B2 | 11/2015 | Overes et al. | |
| 9,173,651 B2 | 11/2015 | Stone et al. | |
| 9,173,653 B2 | 11/2015 | Bojarski et al. | |
| 9,220,493 B2 | 12/2015 | Hart et al. | |
| 9,220,494 B2 | 12/2015 | Bojarski et al. | |
| 9,247,935 B2 | 2/2016 | George et al. | |
| 9,277,914 B2 | 3/2016 | Wales et al. | |
| 9,289,201 B2 | 3/2016 | Schwartz et al. | |
| 9,295,461 B2 | 3/2016 | Bojarski et al. | |
| 9,332,980 B2 | 5/2016 | George et al. | |
| 9,351,722 B2 | 5/2016 | Koogle, Jr. et al. | |
| 9,962,493 B2 * | 5/2018 | Guthart | A61M 5/31501 |
| 2002/0019649 A1 * | 2/2002 | Sikora | A61B 17/0401 606/232 |
| 2002/0116012 A1 | 8/2002 | May et al. | |
| 2002/0143342 A1 | 10/2002 | Hangody et al. | |
| 2002/0193811 A1 | 12/2002 | Chan | |
| 2003/0004467 A1 * | 1/2003 | Musick | A61M 5/284 604/218 |
| 2003/0021827 A1 | 1/2003 | Malaviya et al. | |
| 2003/0023316 A1 | 1/2003 | Brown et al. | |
| 2003/0032961 A1 | 2/2003 | Pelo et al. | |
| 2003/0033021 A1 | 2/2003 | Plouhar et al. | |
| 2003/0036797 A1 | 2/2003 | Malaviya et al. | |
| 2003/0036801 A1 | 2/2003 | Schwartz et al. | |
| 2003/0049299 A1 | 3/2003 | Malaviya et al. | |
| 2003/0078617 A1 | 4/2003 | Schwartz et al. | |
| 2003/0088271 A1 * | 5/2003 | Cragg | A61B 17/0057 606/213 |
| 2003/0130694 A1 * | 7/2003 | Bojarski | A61B 17/0401 606/228 |

(56) References Cited

U.S. PATENT DOCUMENTS

| | | |
|---|---|---|
| 2003/0158604 A1 | 8/2003 | Cauthen et al. |
| 2003/0181928 A1 | 9/2003 | Vidlund et al. |
| 2003/0204194 A1 | 10/2003 | Bittar |
| 2003/0236535 A1 | 12/2003 | Onuki et al. |
| 2004/0002734 A1* | 1/2004 | Fallin .............. A61B 17/0401 606/232 |
| 2004/0015186 A1 | 1/2004 | Bittar |
| 2004/0122450 A1* | 6/2004 | Oren ............... A61B 17/0469 606/148 |
| 2004/0127915 A1* | 7/2004 | Fleenor ........... A61B 17/0469 606/144 |
| 2004/0138683 A1* | 7/2004 | Shelton ........... A61B 17/0401 606/151 |
| 2004/0153074 A1* | 8/2004 | Bojarski .......... A61B 17/0401 606/232 |
| 2004/0166169 A1 | 8/2004 | Malaviya et al. |
| 2004/0225183 A1 | 11/2004 | Michlitsch et al. |
| 2004/0243178 A1 | 12/2004 | Haut et al. |
| 2004/0249395 A1 | 12/2004 | Mikkaichi et al. |
| 2004/0254598 A1* | 12/2004 | Schumacher ...... A61B 17/0467 606/170 |
| 2004/0260343 A1 | 12/2004 | Leclair |
| 2005/0004575 A1* | 1/2005 | Sgro ................ A61B 17/064 606/220 |
| 2005/0033325 A1 | 2/2005 | May et al. |
| 2005/0033363 A1* | 2/2005 | Bojarski .......... A61B 17/0401 606/228 |
| 2005/0090840 A1 | 4/2005 | Gerbino et al. |
| 2005/0113851 A1* | 5/2005 | Swain .............. A61B 17/0401 606/151 |
| 2005/0131313 A1* | 6/2005 | Mikulka ........... A61B 10/0266 600/567 |
| 2005/0159762 A1* | 7/2005 | Nuutinen .......... A61B 17/0401 606/148 |
| 2005/0165418 A1 | 7/2005 | Chan |
| 2005/0187577 A1* | 8/2005 | Selvitelli ......... A61B 17/0401 606/232 |
| 2005/0283192 A1* | 12/2005 | Torrie .............. A61B 17/0401 606/228 |
| 2005/0283246 A1 | 12/2005 | Cauthen et al. |
| 2006/0025819 A1 | 2/2006 | Nobis et al. |
| 2006/0030884 A1 | 2/2006 | Yeung et al. |
| 2006/0064126 A1 | 3/2006 | Fallin et al. |
| 2006/0074438 A1 | 4/2006 | Chan |
| 2006/0100643 A1 | 5/2006 | Laufer et al. |
| 2006/0161183 A1 | 7/2006 | Sauer |
| 2006/0189993 A1 | 8/2006 | Stone |
| 2006/0190042 A1 | 8/2006 | Stone et al. |
| 2006/0265042 A1 | 11/2006 | Catanese et al. |
| 2006/0293709 A1 | 12/2006 | Bojarski et al. |
| 2007/0027476 A1 | 2/2007 | Harris et al. |
| 2007/0049929 A1 | 3/2007 | Catanese et al. |
| 2007/0083236 A1 | 4/2007 | Sikora et al. |
| 2007/0088390 A1 | 4/2007 | Paz et al. |
| 2007/0142846 A1* | 6/2007 | Catanese, III ..... A61B 17/0469 606/142 |
| 2007/0173865 A1 | 7/2007 | Oren et al. |
| 2007/0213746 A1 | 9/2007 | Hahn et al. |
| 2007/0219567 A1 | 9/2007 | Bayer et al. |
| 2007/0270889 A1 | 11/2007 | Conlon et al. |
| 2008/0009904 A1 | 1/2008 | Bourque et al. |
| 2008/0021484 A1 | 1/2008 | Catanese et al. |
| 2008/0021485 A1 | 1/2008 | Catanese et al. |
| 2008/0033232 A1 | 2/2008 | Catanese et al. |
| 2008/0033456 A1 | 2/2008 | Catanese et al. |
| 2008/0033458 A1 | 2/2008 | McLean et al. |
| 2008/0033487 A1 | 2/2008 | Schwartz et al. |
| 2008/0033488 A1 | 2/2008 | Catanese et al. |
| 2008/0039872 A1 | 2/2008 | Catanese et al. |
| 2008/0039893 A1 | 2/2008 | McLean et al. |
| 2008/0188893 A1 | 8/2008 | Selvitelli et al. |
| 2009/0062854 A1 | 3/2009 | Kaiser et al. |
| 2010/0010497 A1 | 1/2010 | Goble et al. |
| 2010/0036414 A1* | 2/2010 | Cragg ............... A61B 17/0057 606/213 |
| 2010/0114161 A1 | 5/2010 | Bojarski et al. |
| 2011/0009872 A1 | 1/2011 | Mistry et al. |
| 2013/0030463 A1 | 1/2013 | Harris et al. |
| 2013/0144314 A1 | 6/2013 | Bojarski et al. |
| 2013/0144337 A1 | 6/2013 | Stone et al. |
| 2013/0204276 A1 | 8/2013 | Stone et al. |
| 2013/0211452 A1 | 8/2013 | Stone et al. |
| 2014/0135835 A1 | 5/2014 | Stone et al. |
| 2014/0214053 A1 | 7/2014 | Bourque et al. |
| 2014/0243858 A1 | 8/2014 | Bourque et al. |
| 2014/0276987 A1 | 9/2014 | Saliman |
| 2014/0296913 A1 | 10/2014 | Orphanos et al. |
| 2014/0350599 A1 | 11/2014 | Torrie et al. |
| 2015/0066061 A1 | 3/2015 | Caborn et al. |
| 2015/0190129 A1 | 7/2015 | Nelson et al. |
| 2015/0223803 A1 | 8/2015 | Trawick |
| 2016/0022261 A1 | 1/2016 | Stone et al. |
| 2016/0120535 A1 | 5/2016 | Ferragamo et al. |
| 2016/0120536 A1 | 5/2016 | Bojarski et al. |

FOREIGN PATENT DOCUMENTS

| | | |
|---|---|---|
| EP | 0241240 A2 | 10/1987 |
| EP | 0415915 A1 | 3/1991 |
| EP | 0702933 A1 | 3/1996 |
| EP | 1408848 A1 | 4/2004 |
| EP | 1685802 A1 | 8/2006 |
| EP | 2098172 A1 | 9/2009 |
| GB | 2118474 A | 11/1983 |
| JP | 2004508128 A | 3/2004 |
| JP | 2004515273 A | 5/2004 |
| WO | 8603666 A1 | 7/1986 |
| WO | 8701270 A1 | 3/1987 |
| WO | 2004037094 A2 | 5/2004 |
| WO | 2006086275 A2 | 8/2006 |
| WO | 2008021691 A2 | 2/2008 |
| WO | 2009014996 A2 | 1/2009 |
| WO | 2009124215 A1 | 10/2009 |
| WO | 2012072244 A1 | 6/2012 |
| WO | 1399671 A1 | 7/2013 |
| WO | 2014039610 A1 | 3/2014 |

OTHER PUBLICATIONS

David Caborn, M.D., "Meniscal Repair with the FasT-Fix Suture System," A Smith & Nephew Technique Plus Illustrated Guide, Smith & Nephew (Andover, MA), (2002), 12 pages.

Arthrotek, "Hand Instruments, HP High Performance, PS Precision Series," Arthrotek, a Biomet Company, Arthrotek, Inc. (Warsaw, IN), (2000), 3 pages.

Borden, Peter, et al., "Biomechanical Comparison of the FasT-Fix Meniscal Repair Suture System with Vertical Mattress Sutures and Meniscus Arrows," The American Journal of Sports Medicine, American Orthopaedic Society for Sports Medicine. vol. 31(No. 3), p. 374-378. (2003).

Caborn, David, "Meniscal Repair with the FasT-Fix Suture System," A Smith & Nephew Technique Plus Illustrated Guide, Smith & Nephew (Andover, MA), (2002), 12 pages.

Fromm, Stuart E., "Surgical Technique for Repair of Meniscal Tears," RapidLoc Meniscal Repair System, Mitek Products (Rapid City, South Dakota), (2001), 6 pages.

Japanese Office Action dated May 13, 2011, for Japanese Patent Application No. 2007-554285 with translation.

International Search Report and Written Opinion Issued in PCT/US2007/074491, dated Aug. 6, 2008.

International Search Report issued in PCT/US06/04039, dated Sep. 13, 2007, 3 pages.

Written Opinion of the International Search Authority in PCT/US06/04039, dated Sep. 13, 2007, 5 pages.

Stone et al. Regeneration of Meniscal Cartilage with Use of a Collagen Scaffold, Analysis of Preliminary Data. The Journal of Bone and Joint Surgery Dec. 1997, 79-A(12); 1770-1777; Abstract.

(56) References Cited

OTHER PUBLICATIONS

Supplementary European Search Report dated Apr. 12, 2013, for EP 06720310, 4 pages.
Patent Examination Report No. 1 from AU 2007284219 dated Aug. 18, 2012, 4 pages.
De Beer, J.F. et al.: 'Nicky's Knot—A New Slip Knot for Arthroscopic Surgery' Arthroscopy: The Journal of Arthroscopic and Relate Surgery vol. 14, No. 1, 1998, pp. 109-110.
Fleega, B.A. et al.: 'The Giant Knot: A New One-Way Self-Locking Secured Arthroscopic Slip Knot' Arthroscopy: The Journal of Arthroscopic and Relate Surgery vol. 15, No. 4, 1999, pp. 451-452.
Nottage, W.M. et al.: 'Arthroscopic Knot Tying Techniques' Arthroscopy: The Journal of Arthroscopic and Relate Surgery vol. 15, No. 5, 1999, pp. 515-521.
Kim, S. et al.: 'The SMC Knot—A New Slip Knot With Locking Mechanism' Arthroscopy: The Journal of Arthroscopic and Relate Surgery vol. 16, No. 5, 2000, pp. 563-565.
Field, M.H. et al.: 'Technical Note: A 'New' Arthroscopic Sliding Knot' Orthopedic Clinics of North America vol. 32, No. 3, 2001, pp. 525-526.
Kim, S. et al.: 'Arthroscopic Knot Tying' Techniques in Shoulder & Elbow Surgery vol. 4, No. 2, 2003, pp. 35-43.
Pallia, C.S: 'The PC Knot: A Secure and Satisfying Arthroscopic Slip Knot' Arthroscopy: The Journal of Arthroscopic and Relate Surgery vol. 19, No. 5, 2003, pp. 558-560.
Wiley, W.B. et al: 'The Tuckahoe Knot: A Secure Locking Slip Knot' Arthroscopy: The Journal of Arthroscopic and Relate Surgery vol. 20, No. 5, 2004, pp. 556-559.
Supplementary European Search Report dated Apr. 25, 2013, for EP 07799856, 3 pages.

\* cited by examiner

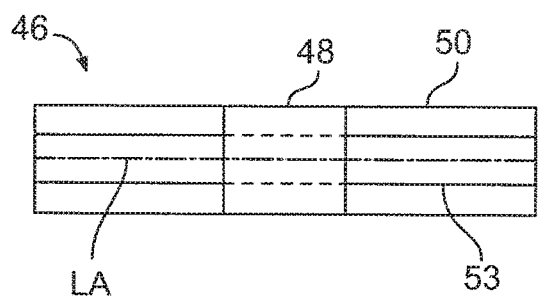 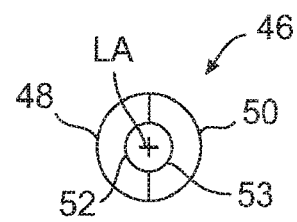
FIG. 9     FIG. 10
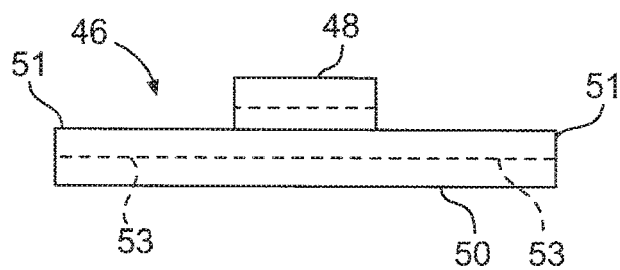
FIG. 11
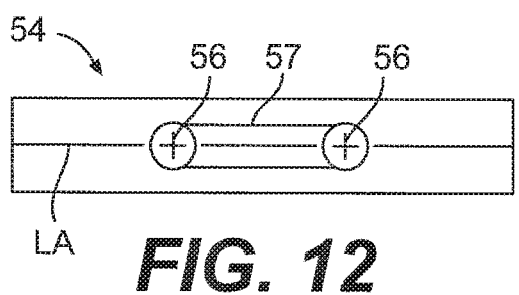 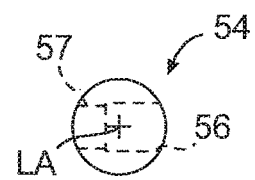
FIG. 12     FIG. 13
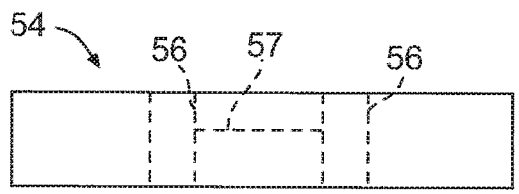
FIG. 14

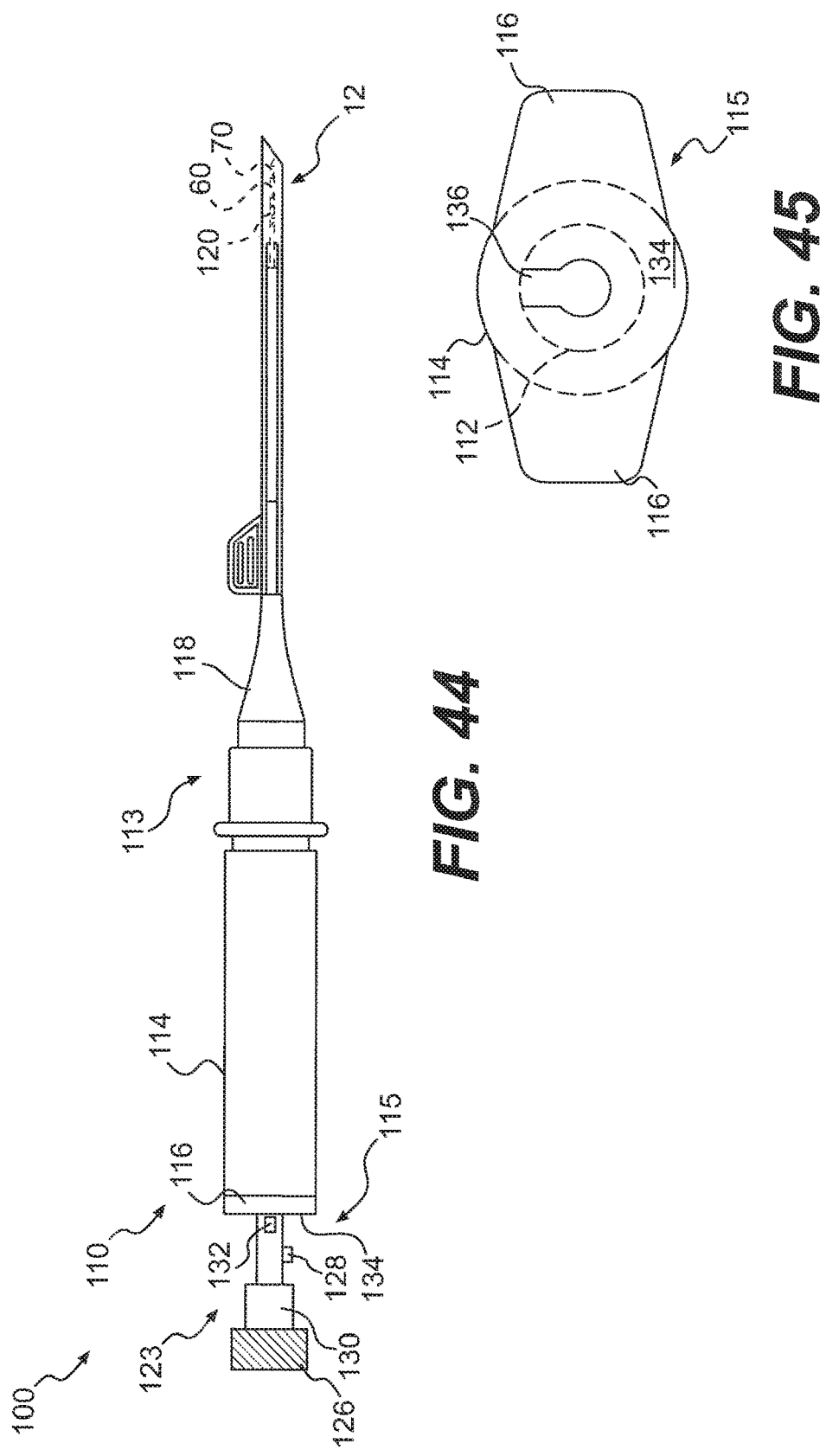

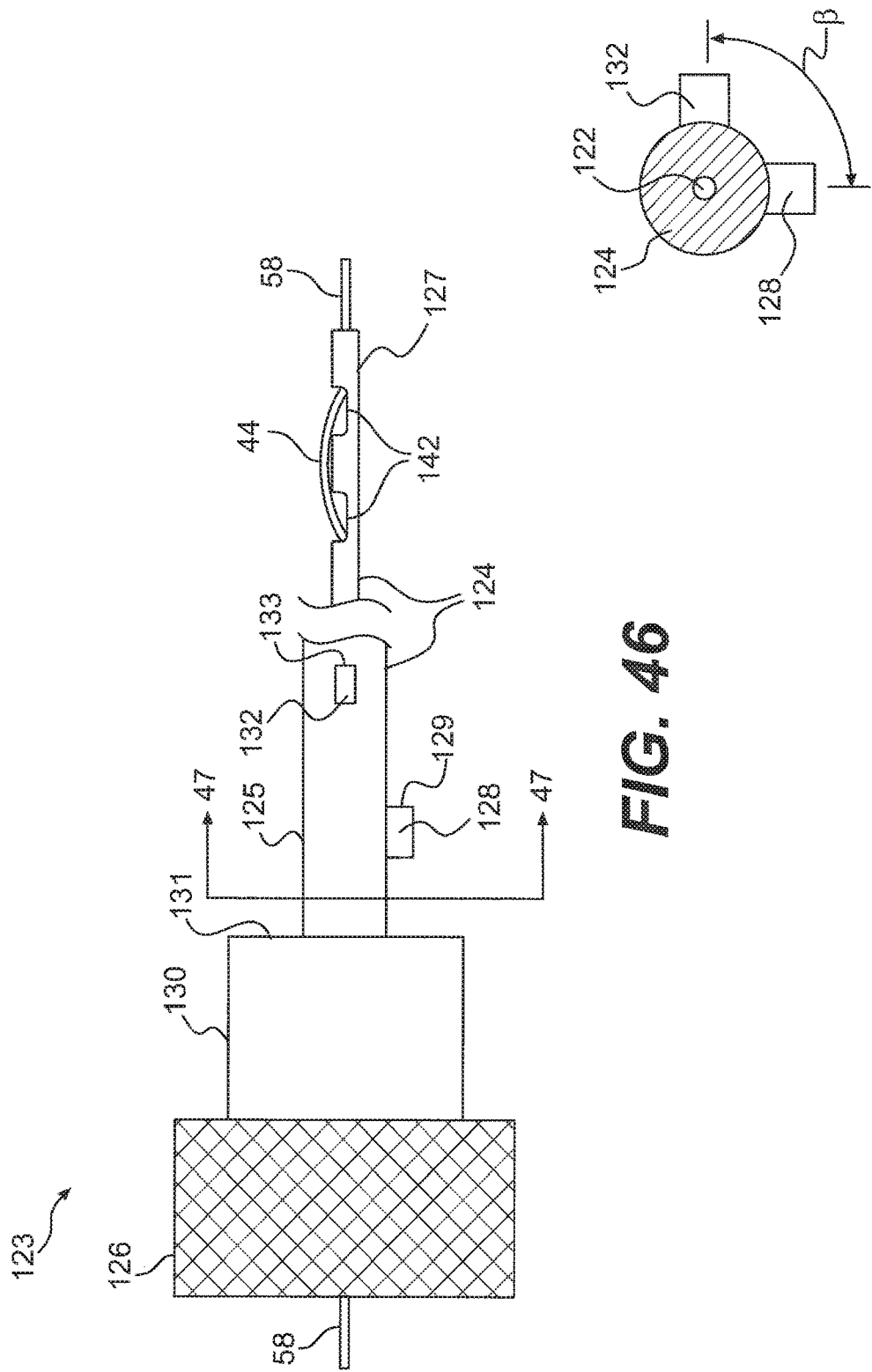

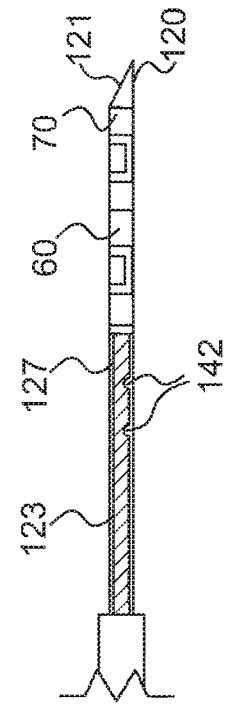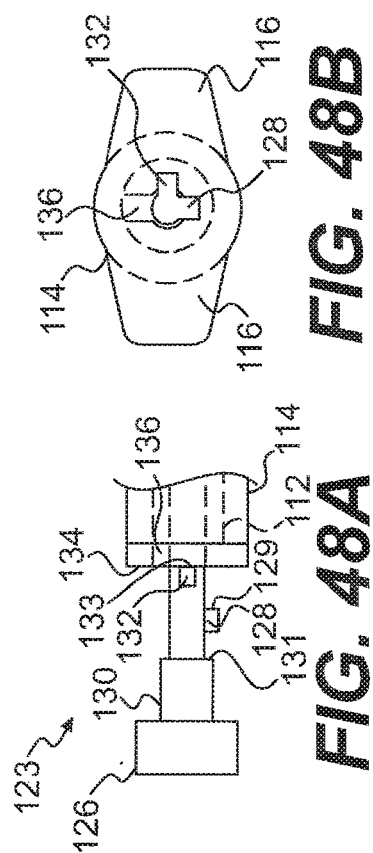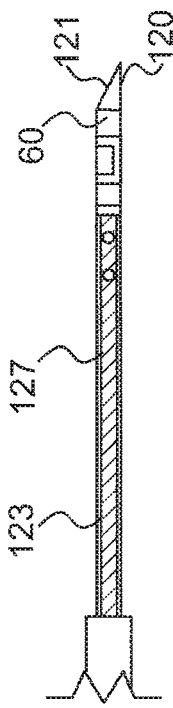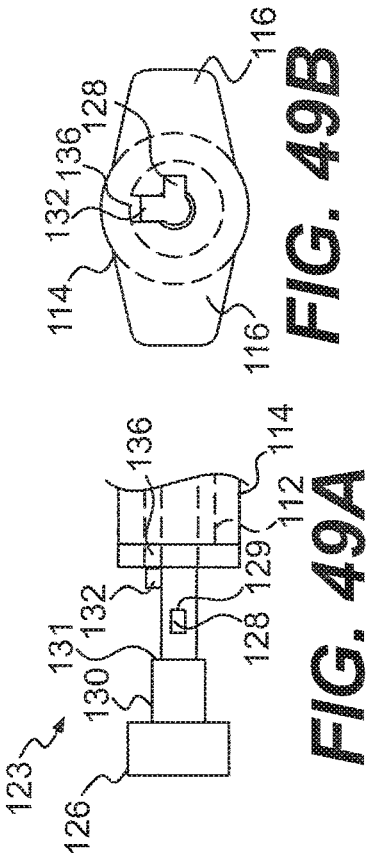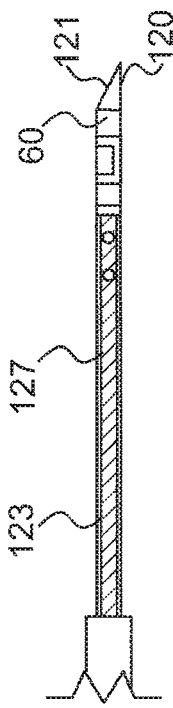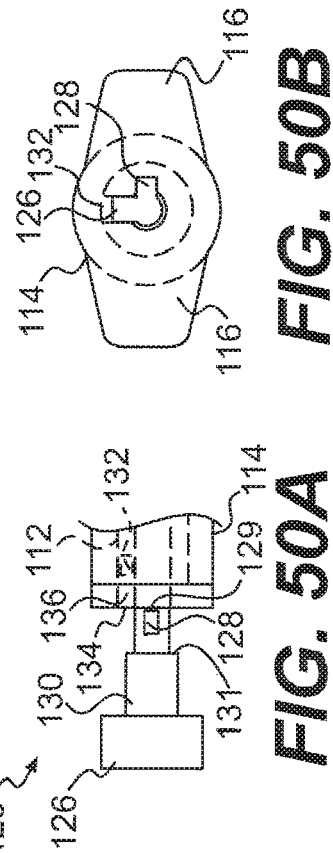

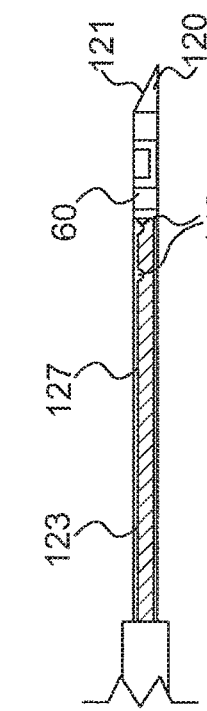 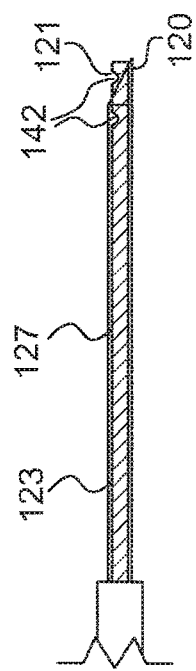 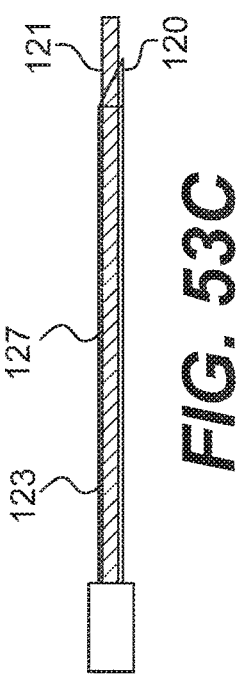
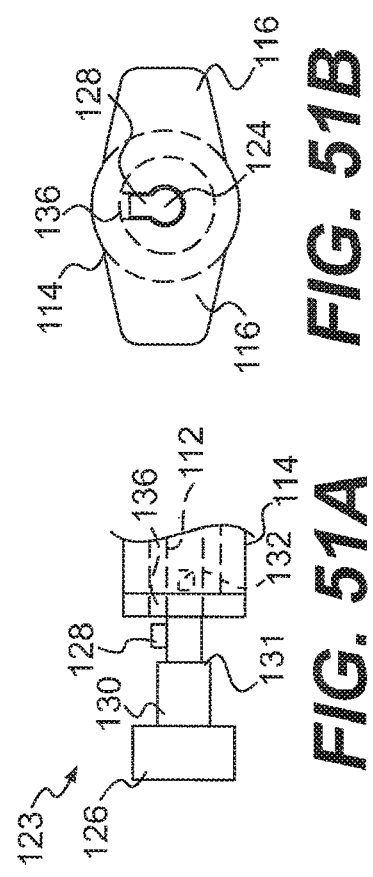 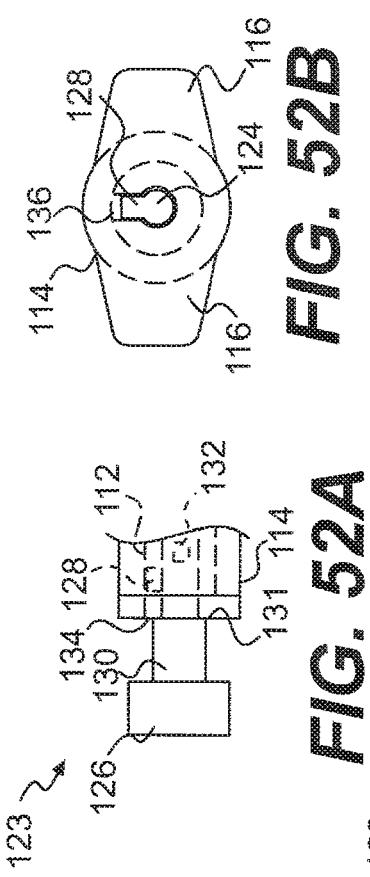 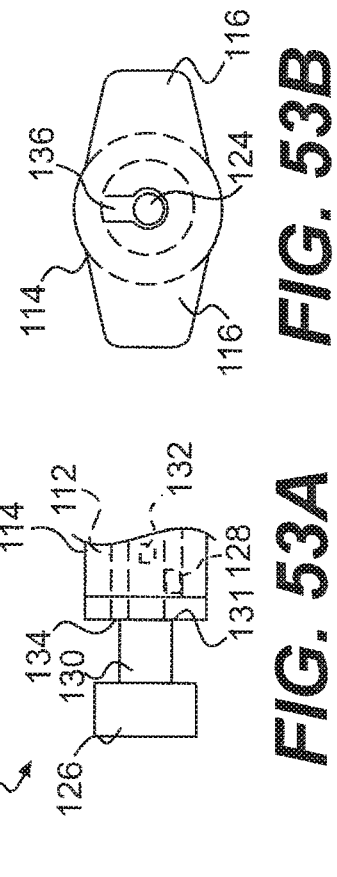

SYSTEM AND METHOD FOR ALL-INSIDE SUTURE FIXATION FOR IMPLANT ATTACHMENT AND SOFT TISSUE REPAIR

REFERENCE TO PENDING PRIOR PATENT APPLICATIONS

This patent application is a continuation of pending prior U.S. patent application Ser. No. 13/410,501, filed Mar. 2, 2012 by Stephen Vaughan Harris et al. for SYSTEM AND METHOD FOR ALL-INSIDE SUTURE FIXATION FOR IMPLANT ATTACHMENT AND SOFT TISSUE REPAIR, now U.S. Pat. No. 9,402,616, which in turn is a continuation of prior U.S. patent application Ser. No. 11/501,235, filed Aug. 9, 2006 by Stephen Vaughan Harris et al. for SYSTEM AND METHOD FOR ALL-INSIDE SUTURE FIXATION FOR IMPLANT ATTACHMENT AND SOFT TISSUE REPAIR, now U.S. Pat. No. 8,128,640, which in turn is a continuation-in-part of prior U.S. patent application Ser. No. 11/348,467, filed Feb. 7, 2006 by Nadine Beverly Nelson et al. for SYSTEM AND METHOD FOR ALL-INSIDE SUTURE FIXATION FOR IMPLANT ATTACHMENT AND SOFT TISSUE REPAIR, now U.S. Pat. No. 8,808,309, which patent application claims benefit of prior U.S. Provisional Patent Application Ser. No. 60/650,131, filed Feb. 7, 2005 by Stephen Harris et al. for SYSTEM AND METHOD FOR ALL-INSIDE SUTURE FIXATION FOR IMPLANT ATTACHMENT AND SOFT TISSUE REPAIR.

BACKGROUND

Field of the Invention

The present invention relates generally to a system and method for attaching an implant during meniscal repair and for other soft tissue repair. More particularly, the present invention relates to a system and method for an all-inside suture fixation device and method designed for the placement of surgical anchors for the attachment of an implant to the meniscus and for soft tissue repair. The present invention also relates to a system designed to reduce, or bring into close approximation, pieces of torn or damaged soft tissue to facilitate tissue repair and healing.

Description of Related Art

There are current procedures for surgical attachment of a soft tissue implant in a joint, such as an autograft, allograft, or xenograft tissue or other compatible tissues and/or devices. Such implants may be bioresorbable and/or non-resorbable, synthetic and/or non-synthetic. One example of a bioresorbable implant is the ReGen® CMI™, a collagen-based meniscus implant, the surgical attachment of which can involve techniques that are difficult to master. There is a need therefore, for a fixation device to facilitate a faster, easier to use method for attaching an implant to a host tissue. Suture fixation devices, such as the FAST-FIX™ and RAPIDLOC™, which were designed to repair tears in meniscus tissue, have certain limitations in their delivery of anchors to attach an implant to the meniscal rim in that they may cause unnecessary destruction to the implant and require additional instruments and steps that are not integral to the device itself. The needle used to pass the anchor through an implant and through the meniscal rim punctures the implant in a manner that may lead to tearing of the implant matrix. There is a need, therefore, for a dimensionally smaller device that employs a smaller needle that delivers a less destructive anchor through an implant and the meniscus, thereby reducing the size of the puncture hole in the implant and the potential for tearing the implant matrix.

There is a need, therefore, for a fixation device that includes an integrated knot pusher to secure the delivered anchor, and optionally, also includes a suture cutter for use after one or more anchors have been secured. Techniques that require separate instruments for knot pushing and suture cutting are less efficient, and require greater skill, time, and additional manipulation at the surgical site.

Prior art devices and methods for suture fixation of an implant to soil tissue within a joint typically tear the matrix of the implant during needle insertion and/or anchor delivery. There remains a need for a device and method for fixing an implant to soft tissue that can insert anchors through the implant and host tissue with minimal destruction of the implant, in a well-controlled and easy manner. Also, there remains a need for a device and method for fixing a collagen-based meniscus implant to the host meniscal tissue, in a well-controlled and easy manner, whereby the needle and anchor insertion cause minimal to no destruction of the collagen-based meniscus implant. Also, there remains a need for a device and method for fixing a collagen-based meniscus implant to the host meniscal tissue that puts adequate tension between the anchors in a ell-controlled and easy manner.

BRIEF SUMMARY OF THE INVENTION

The fixation delivery system of the present invention is an integrated design for use with the multiple elements required for suture fixation when attaching a soft tissue implant to host tissue or when performing tissue repair procedures in general. The present system and method achieves the deployment of anchors into soft tissue and knot pushing with the use of a single instrument, and, optionally, may also provide for suture cutting within that single instrument. The hollow needle applicator and anchors are of smaller dimensions than current applicators and anchors to minimize the damage to the implant during needle insertion and anchor deployment.

The fixation delivery system of the present invention is an integrated design for use with the multiple elements required fir suture fixation when attaching a soft tissue implant to host tissue or when performing tissue repair procedures in general. The present system and method achieves the deployment of anchors into soft tissue and knot pushing with the use of a single instrument, and, optionally, may also provide for suture cutting within that single instrument. The hollow needle applicator and anchors are of smaller dimensions than current applicators and anchors to minimize the damage to the implant during needle insertion and anchor deployment.

In an embodiment of the invention, the applicator for deployment of the anchors includes a hollow needle or cannula having a longitudinal extending bore and an open end, into which a suture, which includes two surgical anchors, is loaded. The first anchor and the second anchor are connected via a flexible portion of the suture. The flexible portion includes a self-locking slide knot located between the first anchor and the second anchor. The needle is inserted into an incision already made in the patient's body, through the implant, and through the host meniscus to the outside rim of the meniscus, or through the soft tissue requiring repair. Alternatively, the needle may penetrate directly through the patient's skin and into the joint capsule comprising the knee. The first anchor is ejected from the tip of the hollow needle by gripping the handle of the applicator and pulling the trigger, which advances a push rod within the hollow needle. The anchor is released, from the open end of the needle to seat firmly on the surface of the soft tissue or rim of the meniscus (i.e., the meniscus rim). The needle is removed from the initial insertion site and inserted through the implant and through the meniscus or host soft tissue a short distance from the initial insertion point, without removing the needle from the patient's body. The second anchor is deployed by gripping the trigger of the applicator to advance the push rod a second time and release the second anchor. The needle is withdrawn or retracted from the second insertion site, thereby leaving two anchors positioned on the outside rim of the meniscus. The push rod, or pusher, functions as a knot pusher and can be used to push a self-locking slide knot; located on the flexible portion between the first and second anchors, until the knot is flush with the implant. Also, the flexible portion may be tightened by hand until adequate tension is applied to hold the pair of anchors firmly in place. Excess length of the flexible portion/suture can be cut using a cutter, which may be in the form of a suture cutting surface on the applicator. Again, the system is designed so that the deployment of the anchors, the pushing of the self-locking slide knot, and the optional cutting may all be completed without removing the needle from the patient's body.

In an embodiment, a system for repairing a meniscus is provided. The system includes a suture that includes a first anchor, a second anchor, and a flexible portion connecting the first anchor and the second anchor. The flexible portion includes a self-locking slide knot between the first anchor and the second anchor. The system also includes a needle having a longitudinal extending bore and an open end. The bore is configured to receive the first anchor and the second anchor. The system further includes a pusher configured to be movable within the bore of the needle. The pusher is configured to (1) discharge the first anchor and the second anchor, and (2) push the self-locking slide knot after the discharge of the second anchor.

In embodiment, a method for repairing a meniscus is provided. The method includes providing a system for repairing a meniscus. The system includes a suture that includes a first anchor, a second anchor, and a flexible portion connecting the first anchor and the second anchor. The flexible portion includes a self-locking slide knot between the first anchor and the second anchor. The system also includes a needle having a longitudinal extending bore and an open end. The bore is configured to receive the first anchor and the second anchor. The system further includes a pusher configured to be movable within the bore of the needle. The pusher is configured to (1) discharge the first anchor and the second anchor, and (2) push the self-locking slide knot after the discharge of the second anchor. The method also includes providing an implant, passing the needle of the system through the implant and the meniscus at a first location to deliver the first anchor to an opposite side of the meniscus, retracting the needle from the meniscus and the implant, passing the needle of the system through the implant and the meniscus at a second location to deliver the second anchor to the opposite side of the meniscus, and pushing the self-locking slide knot to a surface of the implant.

In an embodiment, a method for repairing a meniscus in a body with an implant and a suture is provided. The method includes inserting a needle through the implant and the meniscus at a first location, delivering a first anchor of the suture to an opposite side of the meniscus, retracting the needle from the meniscus and the implant, inserting the needle through the implant and the meniscus at a second location, and delivering a second anchor of the suture to the opposite side of the meniscus. The second anchor is connected to the first anchor with a flexible portion of the suture. The method also includes pushing a self-locking slide knot located along the flexible portion between the first anchor and the second anchor to a surface of the implant. The delivering of the second anchor and the pushing the self-locking knot are completed without removing the needle from the body.

In an embodiment, a method for repairing a tear in a meniscus in a body with a suture is provided. The method includes inserting a needle through the meniscus at a first location, delivering a first anchor of the suture to an opposite side of the meniscus, retracting the needle from the meniscus, inserting the needle through the meniscus at a second location on an opposite side of the tear as the first location, and delivering a second anchor of the suture to the opposite side of the meniscus. The second anchor is connected to the first anchor with a flexible portion of the suture. The method further includes pushing a self-locking slide knot located along the flexible portion between the first anchor and the second anchor to a surface of the meniscus. The delivering of the second anchor and the pushing of the self-locking knot are completed without removing the needle from the body.

In an embodiment, an applicator for delivering a suture to an implant for repairing a meniscus in a body is provided. The suture includes a first anchor, a second anchor, and a flexible portion that connects the first anchor to the second anchor. The applicator includes a needle having a longitudinal bore. The longitudinal bore is configured to receive the first anchor and the second anchor. The applicator also includes a pusher for pushing the first anchor and the second anchor out of the longitudinal bore of the needle. The pusher is configured to receive the flexible portion therein and expose a portion of the flexible portion of the suture. The applicator also includes a cutting surface configured to cut the suture.

In an embodiment, a system for repairing a meniscus is provided. The system includes a suture that includes a first anchor, a second anchor, and a flexible portion connecting the first anchor and the second anchor. The flexible portion includes a self-locking slide knot between the first anchor and the second anchor. The system also includes a needle having a longitudinal extending bore and an open end. The bore is configured to receive the first anchor and the second anchor. The system also includes a body portion operatively connected to the needle at a distal end of the body portion. The body portion has a lumen. The system further includes a pusher configured to rotate and slide within the lumen of the body portion and the longitudinal extending bore of the needle. The pusher has a first stop surface and a second stop surface. The first stop surface of the pusher is constructed and arranged to engage a proximal end of the body portion after the first anchor has been discharged from the needle by the pusher to prevent the pusher from discharging the second anchor. The second stop surface of the pusher is constructed and arranged to engage the proximal end of the body portion after the second anchor has been discharged from the needle by the pusher.

In embodiment, a method for repairing a meniscus in a body with an implant and a suture is provided. The method includes inserting a needle through the implant and the meniscus at a first location, pushing a pusher in a first orientation to a first position relative to the needle to deliver a first anchor of the suture to an opposite side of the meniscus, and retracting the needle from the meniscus and the implant. The method also includes inserting the needle through the implant and the meniscus at a second location, rotating the pusher from the first orientation to a second orientation relative to the needle, and pushing the pusher in the second orientation to a second position relative to the needle to deliver a second anchor of the suture to the opposite side of the meniscus. The second anchor is connected to the first anchor with a flexible portion of the suture. The method further includes retracting the needle from the meniscus and the implant, pushing a self-locking slide knot located along the flexible portion between the first anchor and the second anchor to a surface of the implant with the pusher, and rotating the pusher from the second orientation relative to the needle to cut the flexible portion of the suture at a location adjacent the self-locking slide knot.

In an embodiment, an applicator for delivering a suture to an implant for repairing a meniscus in a body is provided. The suture includes a first anchor, a second anchor, and a flexible portion that connects the first anchor to the second anchor. The applicator includes a needle having a longitudinal extending bore and an open end. The bore is configured to receive the first anchor and the second anchor. The applicator also includes a body portion operatively connected to the needle at a distal end of the body portion. The body portion has a lumen. The applicator further includes a pusher configured to slide and rotate within the lumen of the body portion and the longitudinal bore of the needle. The pusher has a first stop surface and a second stop surface. The first stop surface of the pusher is constructed and arranged to engage a proximal end of the body portion after the first anchor has been discharged from the needle by the pusher to prevent the pusher from discharging the second anchor. The second stop surface of the pusher is constructed and arranged to engage the proximal end of the body portion after the second anchor has been discharged from the needle by the pusher.

With minor alterations, this anchor delivery system device may be used in other procedures for soft-tissue repair, and most preferably for arthroscopic procedures. Examples include, but are not limited to use in reparative procedures for soft tissue damage in joints, securing tissue grafts, and attaching resorbable implants and synthetic scaffolds to host tissue.

Other aspects, features, and advantages of the present invention will become apparent from the following detailed description, the accompanying drawings, and the appended claims.

BRIEF DESCRIPTION OF THE DRAWINGS

Features of the invention are shown in the drawings, in which like reference numerals designate like elements. The drawings form part of this original disclosure, in which:

FIG. 9 is a top view of an anchor of a suture of the system of FIG. 1;

FIG. 10 is an end view of the anchor of FIG. 9;

FIG. 11 is a side view of the anchor of FIG. 9;

FIG. 12 is a top view of another embodiment of an anchor of the suture for the system of FIG. 1;

FIG. 13 is an end view of the anchor of FIG. 12;

FIG. 14 is a side view of the anchor of FIG. 12;

FIG. 44 is a side view of another embodiment of a system for all-inside suture fixation for implant attachment and soft tissue repair of the present invention;

FIG. 45 is a proximal end view of a body portion of the system of FIG. 44;

FIG. 46 is a side view of an embodiment of a pusher of the system of FIG. 44;

FIG. 47 is a cross-sectional view of the pusher taken along line 47-47 in FIG. 46;

FIG. 48A is a side view of a proximal end of the pusher of FIG. 46 in a first position relative to the body portion;

FIG. 48B is the proximal end view of the body portion with a portion of the pusher in the first position of FIG. 48A;

FIG. 48C is a side view of a needle of the system of FIG. 44 and a distal end of the pusher, with the pusher in the first position of FIG. 48A;

FIG. 49A is a side view of the proximal end of the pusher of FIG. 46 in a second position relative to the body portion;

FIG. 49B is the proximal end view of the body portion with a portion of the pusher in the second position FIG. 49A;

FIG. 49C is a side view of the needle and the distal end of the pusher, with the pusher in the second position of FIG. 49A;

FIG. 50A is a side view of the proximal end of the pusher of FIG. 46 in a third position relative to the body portion;

FIG. 50B is the proximal end view of the body portion with a portion of the pusher in the third position of FIG. 50A;

FIG. 50C is a side view of the needle and the distal end of the pusher, with the pusher in the third position of FIG. 50A;

FIG. 51A is a side view of the proximal end of the pusher of FIG. 46 in a fourth position relative to the body portion;

FIG. 51B is the proximal end view of the body portion with a portion of the pusher in the fourth position of FIG. 51A;

FIG. 51C is a side view of the needle and the distal end of the pusher, with the pusher in the fourth position of FIG. 51A;

FIG. 52A is a side view of the proximal end of the pusher of FIG. 46 in a fifth position relative to the body portion;

FIG. 52B is the proximal end view of the body portion with a portion of the pusher in the fifth position of FIG. 52A;

FIG. 52C is a side view of the needle and the distal end of the pusher, with the pusher in the fifth position of FIG. 52A;

FIG. 53A is a side view of the proximal end of the pusher of FIG. 46 in a sixth position relative to the body portion;

FIG. 53B is the proximal end view of the body portion with a portion of the pusher in the sixth position of FIG. 53A; and FIG. 53C is a side view of the needle and the distal end of the pusher, with the pusher in the sixth position of FIG. 53A.

DETAILED DESCRIPTION OF THE INVENTION

Figure 1:
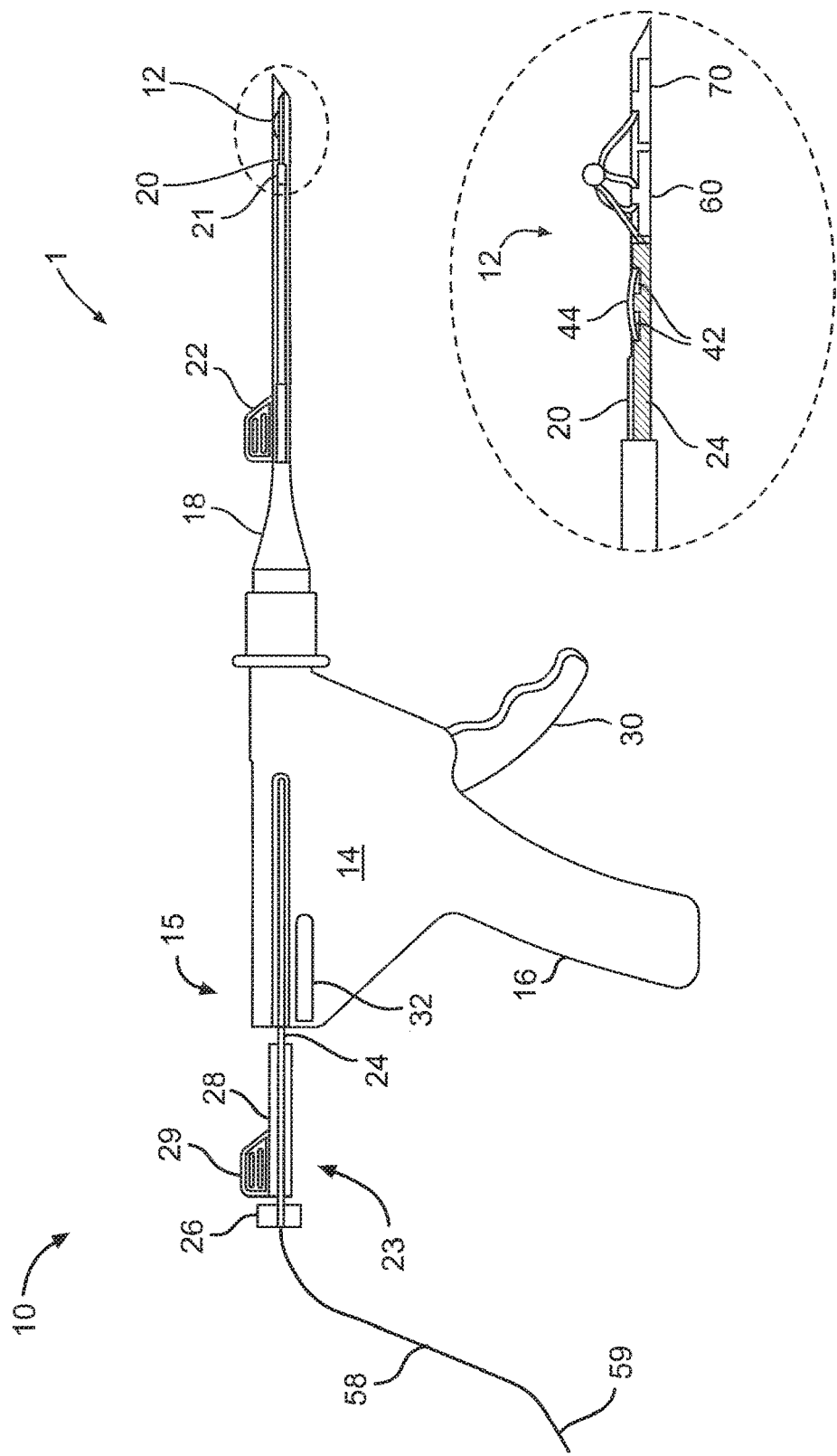
FIG. 1 is a side view of an embodiment of a system for all-inside suture fixation for implant attachment and soft tissue repair of the present invention.

A system 1 for repairing a meniscus according to embodiments of the present invention is illustrated in FIG. 1. The system 1 includes an applicator 10 that is constructed and arranged to deploy a suture 12 to the meniscus. The suture 12 generally includes a flexible portion 58 and a pair of anchors 60, 70. The suture 12 will be discussed in greater detail below.

The applicator 10 includes a body portion 14 that defines a handle 16 that is configured to be grasped by the user. The body portion 14 of the applicator 10 receives a cannula 18 that extends from the body portion 14 in a direction that is away from the handle 16. The body portion 14 and cannula 18 may be constructed and arranged like those described and shown in U.S. Pat. No. 5,928,252, entitled Device and Method for Driving a Needle and Meniscal Repair, which is incorporated herein by reference in its entirety. Because the inner workings of the body portion 14 are not related to the present invention, they are not described in detail herein.

The applicator 10 also includes a needle 20 that is connected to a distal end of the cannula 18 Of course, the needle 20 may be considered to be a part of the cannula 18 itself. The needle 20 will be described in greater detail below. The applicator 10 also includes a pusher 23 that includes a hollow rod 24 that extends through the body portion 14, the cannula 18, and is slidingly received by the needle 20. A knob 26 is attached to one end of the rod 24 and a spacer 28 with a tab 29 is disposed between the knob 26 and a proximal end 15 of the body portion 14 so that the movement of the knob 26 relative to the body portion 14 and, hence, movement of the rod 24 relative to the needle 20, may be limited to prevent premature ejection of one of the anchors 60 prior to the placement of the other anchor 70, as described in further detail below. A trigger 30 is connected to and extends from the body portion 14, as shown in FIG. 1. The trigger 30 is configured to manually control the advancement of the rod 24 within the cannula 18. A side lever 32 is connected to the body portion so as to be pivotable thereon. Operation of the side lever 32 will be discussed in greater detail below.

As shown in FIG. 1, a depth penetration limiter 21 is placed over the distal end of the cannula 18 so as to partially cover the needle 20. The limiter 21 provides the user with a visualization of the depth of the needle 20 in the tissue to avoid neurovascular injury. An outer sheath 22 is placed over the limiter 21 to aid in the insertion of the cannula 18 into the incision already created in the patient. The outer sheath 22 is preferably designed to partially surround the limiter 21 so that the user may still see at least a portion of the limiter 21 when the needle 20 is being inserted into the incision. The outer sheath 22 is removed by the user once the cannula 18 has been inserted into the incision site.

Figure 2:
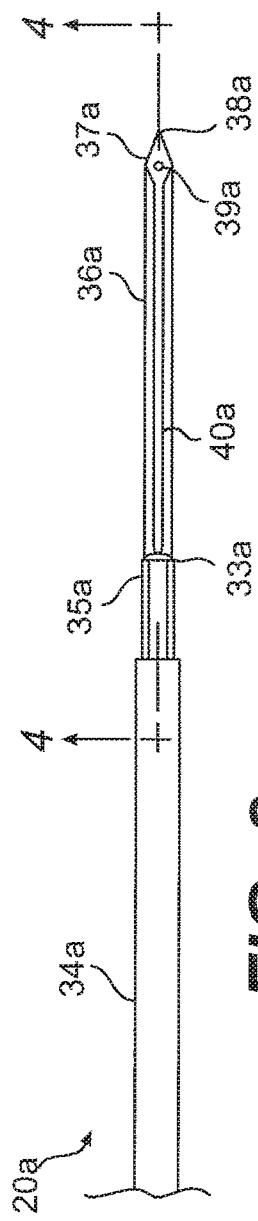
FIG. 2 is a top view of an embodiment of a needle of the system of FIG. 1.
Figure 3:
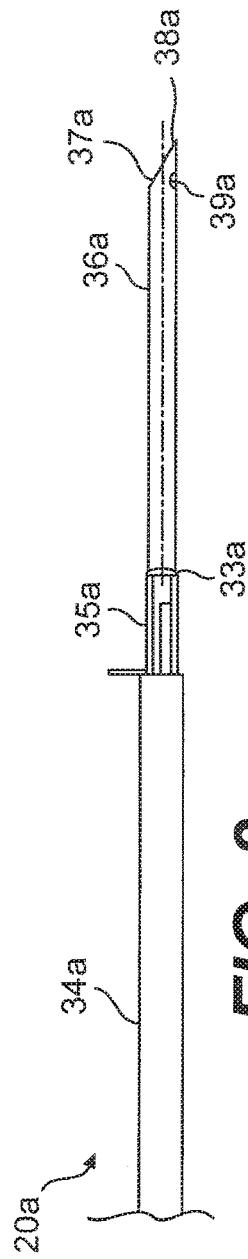
FIG. 3 is a side view of the needle of FIG. 2.
Figure 4:
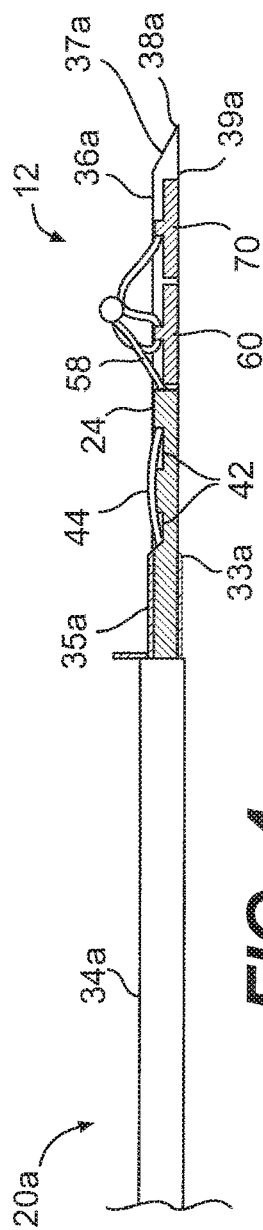
FIG. 4 is a cross-sectional view taken along line 4-4 in FIG. 2.

One embodiment of a needle 20a that may be used as the needle 20 in FIG. 1 is shown in FIGS. 2-4. As shown, the needle 20a includes a sleeve 34a that is attached to the cannula 18 at a proximal end. The needle 20a also includes a distal end 36a that is connected to the sleeve 34a and is constructed and arranged to be inserted into a meniscus or a tissue. The distal end 36a is substantially straight and includes a point 38a for piercing the meniscus or tissue and a slot 40a, which allows for the flexible portion 58 of the suture 12 to extend out of the needle 20a. As shown in the Figures, the distal end 36a of the needle 20a also includes a cutting surface 37a that is constructed and arranged to cut excess suture 12, which will be described in greater detail below.

As shown in FIGS. 2-4, a cutting sheath 35a that at least partially surrounds the distal end 36a may also be provided. In the illustrated embodiment, the cutting sheath 35a completely surrounds the circumference of the distal end 36a. In other embodiments, the cutting sheath 35a may only partially surround the distal end 36a. The cutting Sheath 35a is configured to be slidable relative to the distal end 36a so that it may be moved longitudinally along the distal end 36a toward the point 38a, and then moved back again toward the sleeve 34a. The cutting sheath 35a may include a tab that extends outward from the needle 20a so that the user my manipulate the cutting sheath 35a via the tab. As shown, the cutting sheath 35a includes at least one cutting surface 33a that is constructed and arranged to cut excess suture 12, which will be described in a detail below.

As shown in FIG. 4, the distal end 36a is configured to hold the pair of anchors 60, 70 of the suture 12. The needle 20a may include a dimple 39a located near the point 38a to assist in seating the anchors 60, 70 prior to deployment of the anchors 60, 70 from the needle 20a, as will be described in greater detail below. The needle 20a is preferably manufactured from stainless steel, and is sized to withstand insertion through the implant and the meniscus substantially without bending or buckling.

Figure 5:
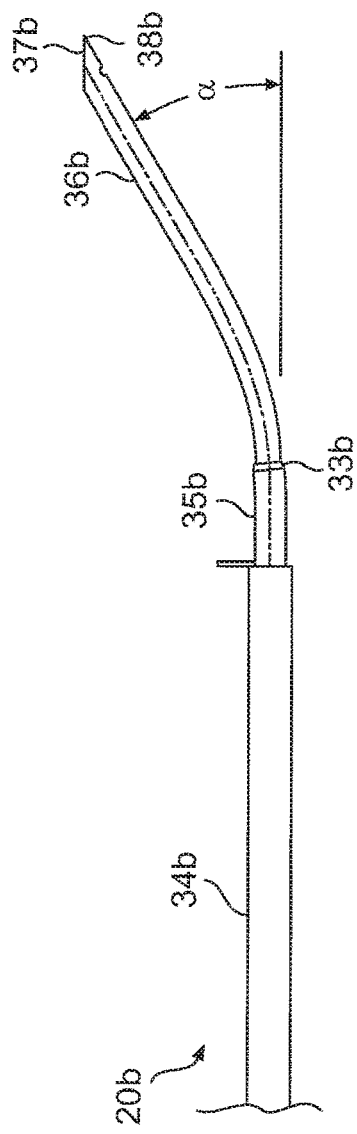
FIG. 5 is a side view of another embodiment of the needle for the system of FIG. 1.
Figure 6:
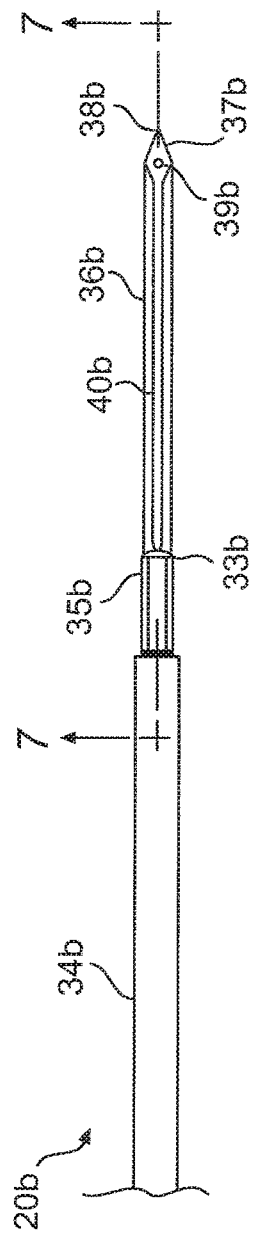
FIG. 6 is a top view of the needle of FIG. 5.
Figure 7:
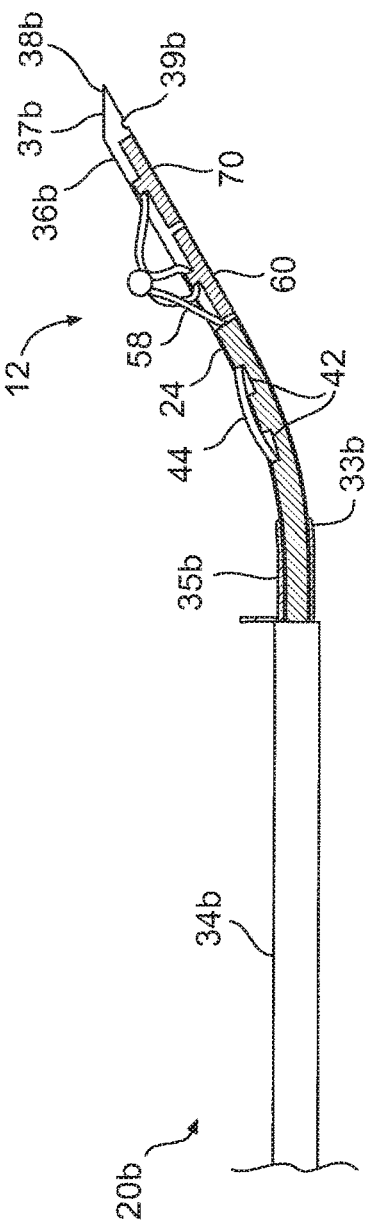
FIG. 7 is a cross-sectional view taken along line 7-7 in FIG. 6.

Another embodiment of a needle 20b that may be used as the needle 20 in the applicator 10 is shown in FIGS. 5-7. As shown, the needle 20b includes a sleeve 34b that is attached to the cannula 18 at a proximal end. The needle 20b also includes a distal end 36b that is connected to the sleeve 34b and is constructed and arranged to be inserted into a meniscus or a tissue. The distal end 36b is curved such that it extends at an angle α relative to the sleeve 34b. The angle α may be about 15-45°, and is preferably about 30°. The distal end 36b also includes a point 38b for piercing the meniscus or tissue and a slot 40b, which allows for portions of the suture 12 to extend out of the needle 20b. The distal end 36b of the needle 20b also includes at least one cutting surface 37b that is constructed and arranged to cut excess suture 12.

As shown in FIGS. 5-7, a cutting sheath 35b that at least partially surrounds the distal end 36b may also be provided. In the illustrated embodiment, the cutting sheath 35b completely surrounds the circumference of the distal end 36b. In other embodiments, the cutting sheath 35b may only partially surrounds the distal end 36b. The cutting sheath 35b is configured to be slidable relative to the distal end 36b so that it may be moved longitudinally along the distal end 36b toward the point 38b, and back again to the sleeve 34b. The cutting sheath 35b may include a tab that extends outward from the needle 20b so that the user my manipulate the cutting sheath 35b via the tab. As shown, the cutting sheath 35b includes a cutting surface 33b that is constructed and arranged to cut excess suture 12.

As shown in FIG. 7, the distal end 36b is also configured to hold the pair of anchors 60, 70. The needle 20b may also include a dimple 39b located near the point 38b to assist in seating the anchors 60, 70 prior to deployment. Like the needle 20a of FIGS. 2-4, the needle 20b is preferably manufactured from stainless steel, and is sized to withstand insertion through the implant and the meniscus substantially without bending or budding.

Figure 8:
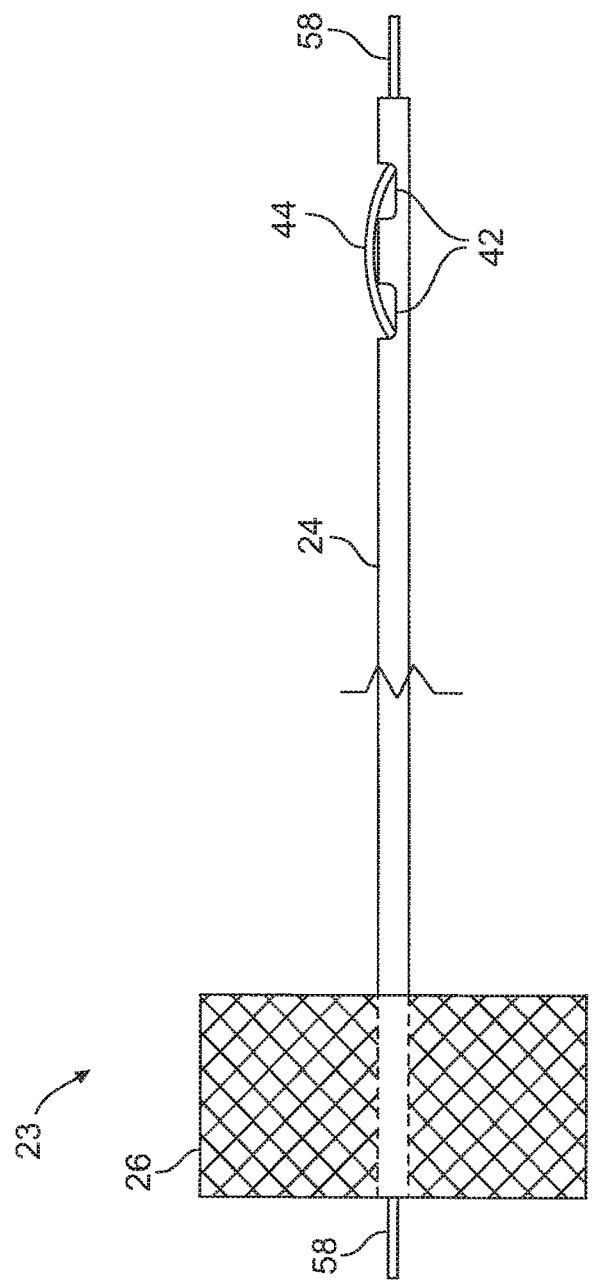
FIG. 8 is a side view of a pusher of the system of FIG. 1.

An embodiment of the pusher 23 is shown in greater detail in FIG. 8. The rod 24 is hollow and is configured to receive the flexible portion 58 of the suture 12 that extends away from the needle 20. The knob 26 includes a hole for receiving the rod 24, so that the flexible portion 58 of the suture 12 may extend through the knob 26 as well. A distal portion of the rod 24 includes a pair of slots 42 that are configured to allow the flexible portion 58 of the suture 12 to be threaded out of the rod 24 via one slot 42 (the distal slot) and back into the rod 24 via the other slot 42 (the proximal slot), as represented by an exposed portion 44 of the flexible portion 58 of the suture 12. This threading of the suture 12 properly aligns the exposed portion 44 relative to the rod 24 to facilitate the cutting of the suture 12, which will be described in further detail below. As shown in FIG. 7, the rod 24 may be flexible so that it may be used with the embodiment of the needle 20b described above.

FIGS. 9-11 illustrated an embodiment of an anchor 46 that may be used as the anchors 60, 70 of the suture 12. As shown, the anchor 46 includes a tab 48 that extends upward from a body 50. The body 50 has opposing ends 51 that are substantially perpendicular to a longitudinal axis LA of the anchor 46. A hole 52 that is centered on the longitudinal axis LA extends through the body 50 and the tab 48 where the body 50 and tab 48 are connected. Otherwise, the body 50 includes a hollowed out half-cylinder 53 at portions where the tab 48 is not connected. The anchor 46 is preferably made out of a bioabsorbable polymer, such as poly(L-lactide).

Another embodiment of an anchor 54 for use in the suture 12 of the system 1 is shown in FIGS. 12-14. As shown, the anchor 54 is a solid rod with a pair of holes 56 that extend substantially perpendicularly through the longitudinal axis of the rod. The holes 56 are sized to receive a flexible portion of the suture 12. A recessed channel 57 is located between the holes 56 to seat the flexible portion 58 of the suture 12. Like the anchor 46, the anchor 54 is preferably made out of a bioabsorbable polymer, such as poly(L-lactide).

In another embodiment of an anchor that may be used as one or both of the anchors 60, 70 of the suture 12, the anchor may include at least one barb that is formed from or connected to a main body portion of the anchor. The barb may be constructed and arranged to be biased to an orientation in which a free end of the barb extends away from the body, yet is oriented such that the free end is near the body when suitable pressure is applied to the barb. The use of such an anchor with the system 1 will be described in greater detail below.

Unless otherwise indicated herein, further discussions of the anchors 60, 70 will be for the anchor 46 illustrated in FIGS. 9-11, although it is understood that the anchor 54 of FIGS. 12-14 may be used with slight modifications to the language used to describe the assembly of the suture 12. Such modifications would be readily appreciated by one of skill in the art and are therefore not described herein.

Figure 15:
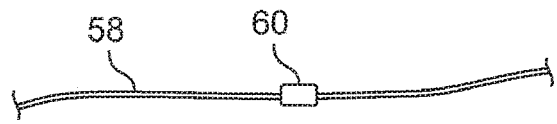
FIG. 15 is a view of an anchor threaded onto a flexible portion of the suture of the system of FIG. 1.
Figure 16:
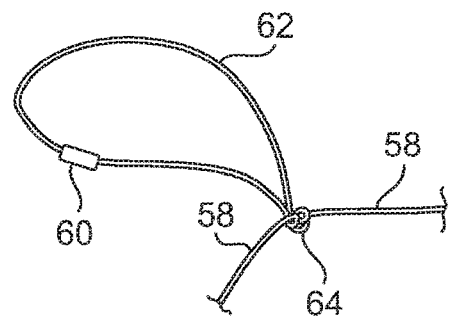
FIG. 16 is a view of the anchor and the flexible portion of FIG. 15 with a loop and a self-locking slide knot formed in the flexible portion.

FIGS. 15-23 show the various stages of an embodiment of assembling the suture 12 of the system 1 of FIG. 1. FIG. 15 shows the flexible portion 58 of the suture 12 with one anchor 60 threaded thereon. FIG. 16 shows a loop 62 and a knot 64 that closes the loop 62, with the anchor 60 being located within the loop 62. The knot 64 is preferably a self-locking slide knot. Methods for tying a self-locking slide knot are described in, for example, "A New Clinch Knot," Weston, P. V., Obstetrics & Gynecology, Vol. 78, pp. 144-47 (1991); "Physical Properties of Self Locking and Conventional Surgical Knots," Israelsson, L. A., et al., European Journal of Surgery, Vol. 160, No. 6-7, pp. 323-27 (1994); "Nicky's Knot—A New Slip Knot for Arthroscopic Surgery," De Beer, J. F., et al., Arthroscopy: The Journal of Arthroscopic and Relate Surgery, Vol. 14, No 1, pp. 109-110 (1998); "The Giant Knot: A New One-Way Self-Locking Secured Arthroscopic Slip Knot," Fleega, B. A., et al., Arthroscopy: The Journal of Arthroscopic and Relate Surgery, Vol. 15, No 4, pp. 451-52 (1999); "Arthroscopic Knot Tying Techniques," Nottage, W. M., et al., Arthroscopy: The Journal of Arthroscopic and Relate Surgery, Vol. 15, No 5, pp. 515-521 (1999); "The SMC Knot—A New Slip Knot With Locking Mechanism," Kiln, S., et al., Arthroscopy: The Journal of Arthroscopic and Relate Surgery, Vol. 16, No 5, pp. 563-65 (2000); "Technical Note: A 'New' Arthroscopic Sliding Knot," Field, M. H., et al., Orthopedic Clinics of North America, Vol. 32, No. 3, pp. 525-26 (2001); "Arthroscopic Knot Tying," Kim, S., et al., Techniques in Shoulder & Elbow Surgery, Vol. 4, No. 2, pp. 35-43 (2003); "The PC Knot: A Secure and Satisfying Arthroscopic Slip Knot," Pallia, C. S., Arthroscopy: The Journal of Arthroscopic and Relate Surgery, Vol. 19, No 5, pp. 558-560 (2003); and "The Tuckahoe Knot: A Secure Locking Slip Knot," Wiley, W. B., et al., Arthroscopy: The Journal of Arthroscopic and Relate Surgery, Vol. 20, No 5, pp. 556-59 (2004), all of which are incorporated herein by reference in their entireties.

Figure 17:
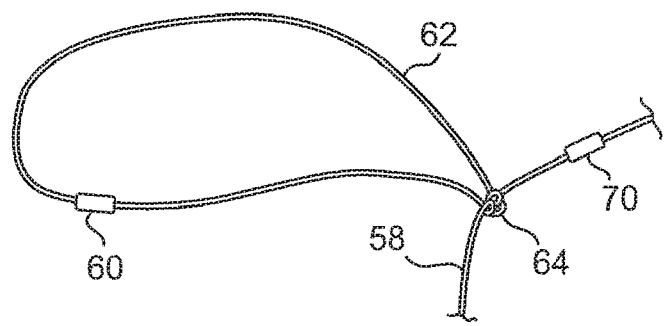
FIG. 17 is a view of the anchor and the flexible portion of FIG. 16 with a second anchor positioned on the flexible portion.
Figure 18:
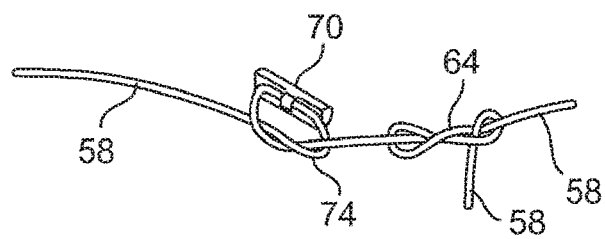
FIG. 18 is a partial view of the second anchor and the flexible portion of FIG. 17.

Once the self-locking slide knot 64 has been tied, another anchor 70 is slid onto the flexible portion 58 until it is located approximately 7 mm from the knot 64, as shown in FIG. 17 (note that the Figures are not necessarily drawn to scale). This distance is only meant to be an example and is not intended to be limiting in any way. The flexible portion 58 of the suture 12 is tied off with one hitch knot 74 on the anchor 70, as shown in FIG. 18.

Figure 19:
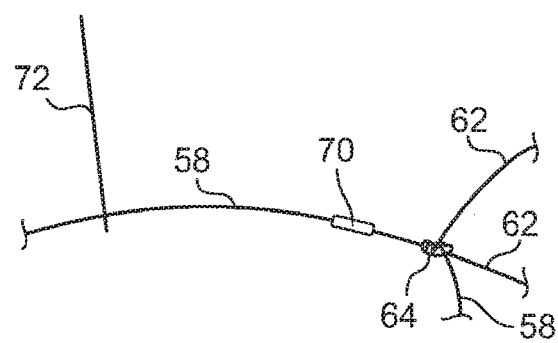
FIG. 19 is a partial view of the second anchor and the flexible portion of FIG. 17 with a needle threaded on the flexible portion.
Figure 20:
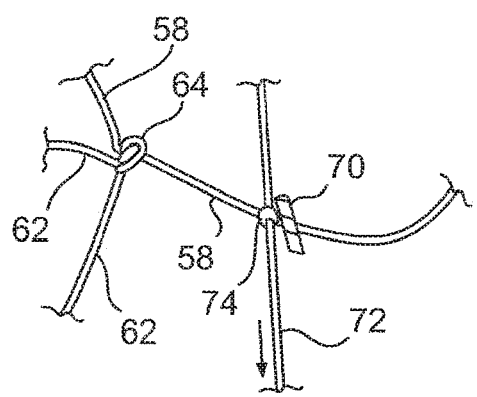
FIG. 20 is a partial view of the needle threaded on the flexible portion and passing through the center of the suture at the second anchor.
Figure 21:
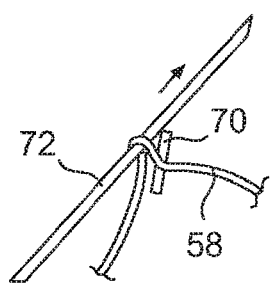
FIG. 21 is a partial view of the needle passing through the center of the suture at the second anchor a second time.
Figure 22:
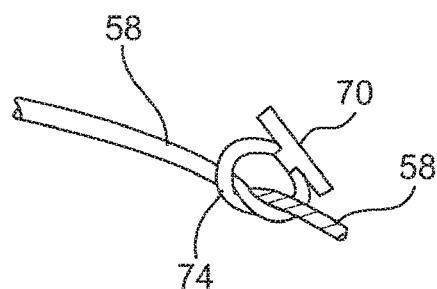
FIG. 22 is a view of the anchor with a knot securing it to the flexible portion.
Figure 23:
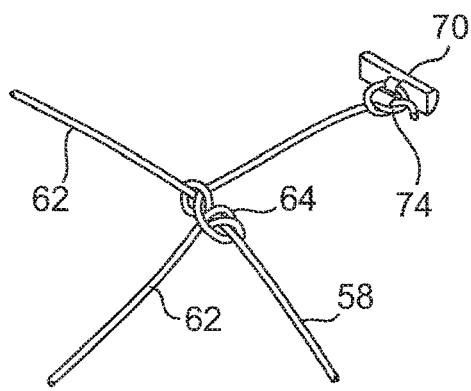
FIG. 23 is a partial view of the flexible portion and the second anchor at one end thereof.
Figure 26:
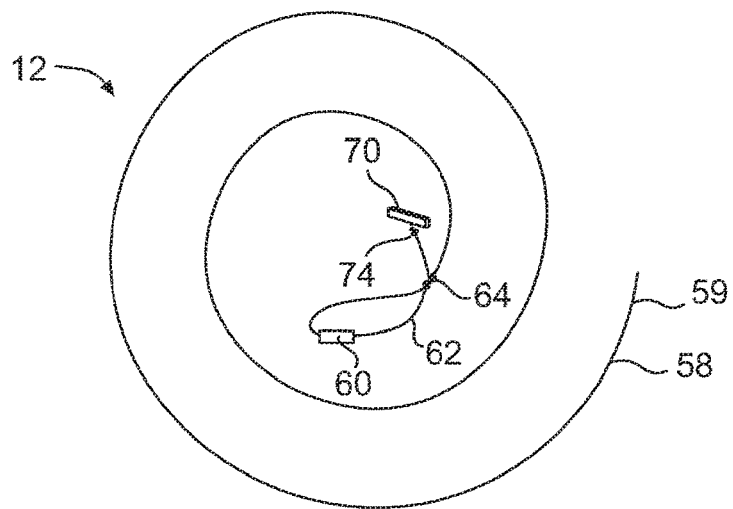
FIG. 26 is a view of the suture of the system of FIG. 1.

Next, as shown in FIG. 19, a needle 72 is threaded with the remainder of the flexible portion 58. The end of the flexible portion 58 with the needle 72 is passed through the center of the suture of the hitch knot twice to hold the hitch knot 74 in place, as shown in FIGS. 20 and 21. As shown in FIG. 22, the excess flexible portion 58 is cut, leaving approximately 2 mm as a tail. Finally, as shown in FIG. 23, the tip of the flexible portion 58 may be melted to prevent fraying of the suture 12. An assembled suture 12 before it is loaded into the applicator 10 is shown in FIG. 26.

Figure 24:
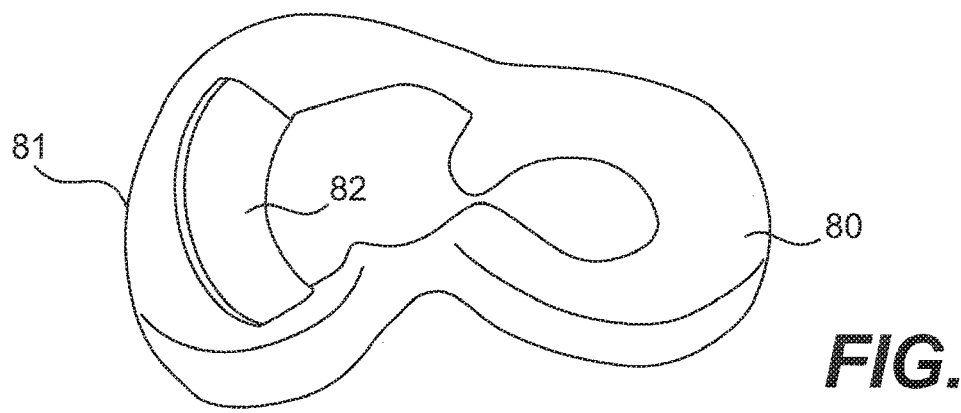
FIG. 24 is a perspective view of a meniscus with an implant positioned on the meniscus.
Figure 25:
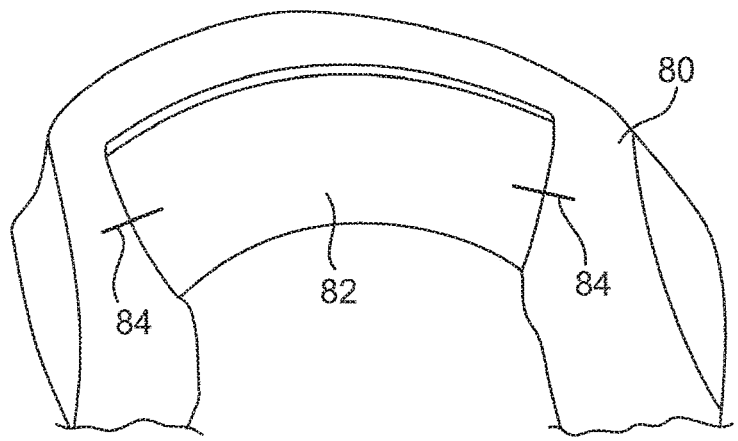
FIG. 25 is a view of the implant after it has been stapled to the meniscus.

FIG. 24 shows a damaged meniscus 80 having a rim 81, and an implant 82 positioned adjacent the damaged part of the meniscus 80. The implant 82 may be any type of implant 82 suitable for such meniscus repair. Preferably, the implant 82 includes collagen. In an embodiment, the implant 82 includes the CMI, a collagen-based meniscus implant. The implant 82 illustrated in the Figures has already been cut to the appropriate size. Both ends of the implant 82 may be temporarily stapled or sutured using conventional means to hold the implant 82 in place while it is being secured to the meniscus 80. FIG. 25 shows a pair of staples 84, or sutures, holding the implant 82 in place.

Figure 27:
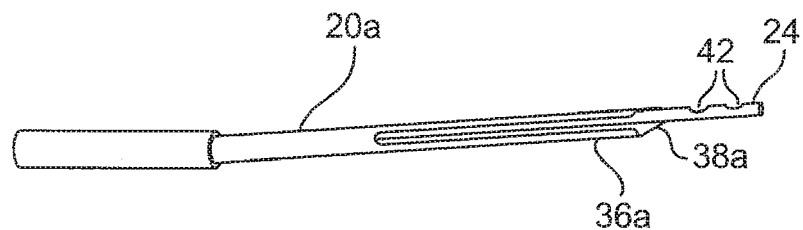
FIG. 27 is a top view of the needle with the pusher extended therefrom.

To load the suture 12 into the applicator 10, the cannula 18, with the needle 20*a* attached, is inserted into the body portion 14 of the applicator 10. In this embodiment, the needle 20*a* of FIGS. 2-4 is shown. However, it is understood that the needle 20*b* may also be used in the same way. The illustrated and described embodiments are not intended to be limiting in any way. While holding down the side lever 32 with a finger or a thumb, the rod 24 of the pusher 23 is inserted by the user into the proximal end 15 of the body portion 14 until the end of the rod 24 extends past the point 38*a* of the needle 20*a* with the slots 42 facing upward, as shown in FIG. 27.

Figure 28:
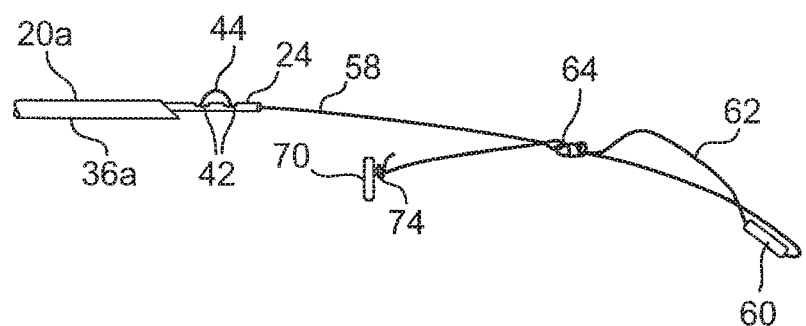
FIG. 28 is a side view of the suture being threaded into the pusher and the needle.
Figure 29:
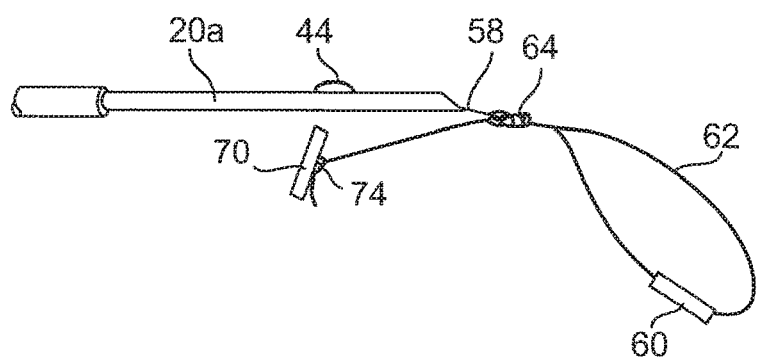
FIG. 29 is a side view of the suture further being threaded into the pusher and the needle.
Figure 30:
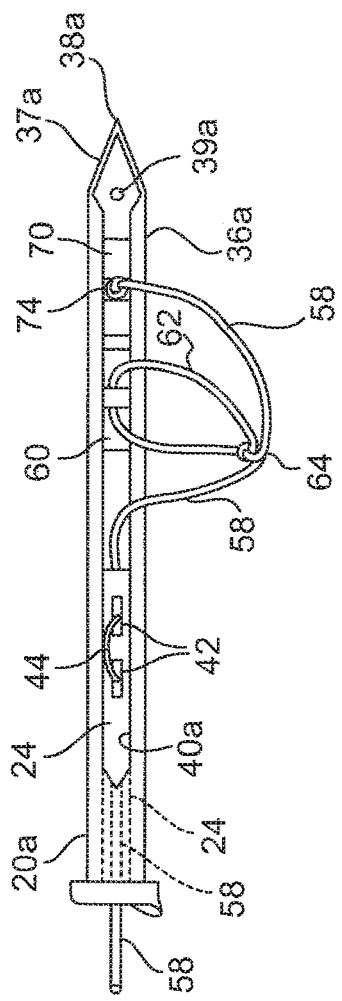
FIG. 30 is a top view of the needle with the suture loaded therein.
Figure 31:
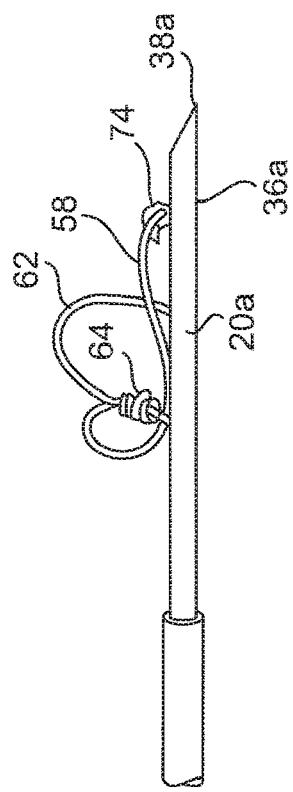
FIG. 31 is a side view of the needle of FIG. 30.

Next, as shown in FIG. 28, an end 59 of the suture 12 that is opposite the anchor 70 is threaded though the rod 24 of the pusher 23 at the distal end 36*a* of the needle 20*a*. The end 59 of the suture 12 is laced through the distal end of the rod 24, pulled out of the rod 24 at the distal slot 42, threaded back into the rod 24 at the proximal slot 42, thereby leaving the exposed portion 44 outside of the rod 24. The end 59 of the suture 12 may extend several inches outside the pusher 23 beyond the proximal end 15 of the body portion 14 of the applicator 10 so that the user may grasp the suture 12 during the implant attachment procedure, which will be described below. Once the suture 12 has been loaded into the applicator 10, the user then presses the side lever 32 and retracts the pusher 23 back into the needle 20*a*, as shown in FIG. 29, to locate the slots 42 and the exposed portion 44 of the suture 12 before the proximal end of the needle slot 40*a*, as shown in FIG. 30. The anchor 60 is inserted into the distal end 36*a* of the needle 20*a*, and is followed by the anchor 70, as shown in FIGS. 30 and 31. The end 59 of the flexible portion 58 that extends out of the pusher 23 at the proximal end 15 of the body portion 14 of the applicator 10 may be pulled so that the knot 64 is generally located on a side of the anchor 60 that is opposite the other anchor 70, as shown in FIG. 31. After the anchors 60, 70 are loaded into the cannula 18, a portion of the flexible portion 58 may extend outside of the cannula 18 via the slot 40*a* of the needle 20*a*, as shown in FIGS. 30 and 31. In this arrangement, the pulling of the trigger 30 causes the anchor 70, the anchor 60, and the knot 64 to be deployed in that order.

Once the system 1 is assembled, the user places the spacer 28 between the knob 26 and the proximal end 15 of the body portion 14 so that the advancement of the anchor 60 will be limited until the placement of the anchor 70 is complete. The user then inserts the depth penetration limiter 21 and the outer sheath 22 over the distal end of the cannula 18 so as to cover the needle 20 during insertion of the needle 20 into the incision site. Once the needle 20 has been inserted into the incision site, the outer sheath 22 may be removed from the cannula 18. Of course, the use of the spacer 28, the outer sheath 22, and the depth penetration limiter 21 should be considered optional. The illustrated embodiment is not intended to be limiting in any way.

The user may then advance the anchors 60, 70 until the anchor 70 is located near the point 38*a* of the needle 20*a*, without extending out of the needle 20*a*. The dimple 39*a* may be used to assist with the placement of the anchor 70. In embodiments where the dimple 39*a* is used, the user should feel a slight resistance to the advancement of the anchor 70, which signals the user to stop advancing the pusher 23. Of course, the use of the dimple 39*a* should be considered to be optional. The illustrated embodiment is not intended to be limiting in any way.

Figure 32:
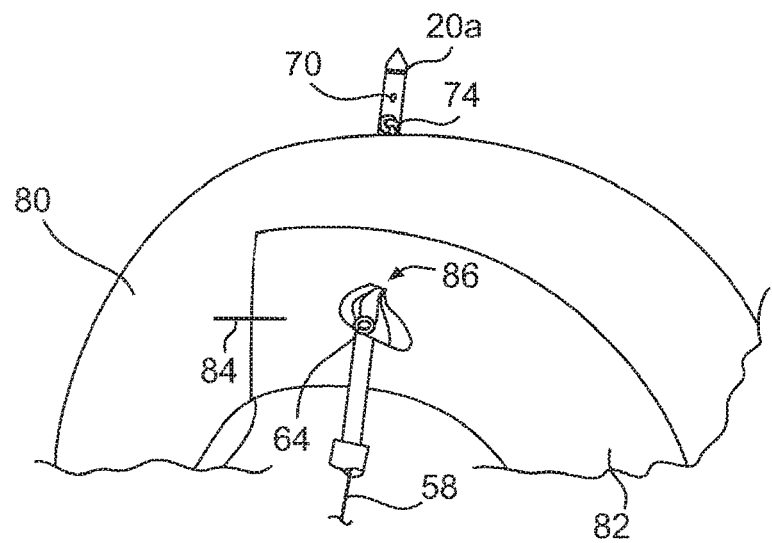
FIG. 32 is a top view of the needle of the system of FIG. 1 piercing the implant and meniscus of FIG. 25 at a first location.
Figure 33:
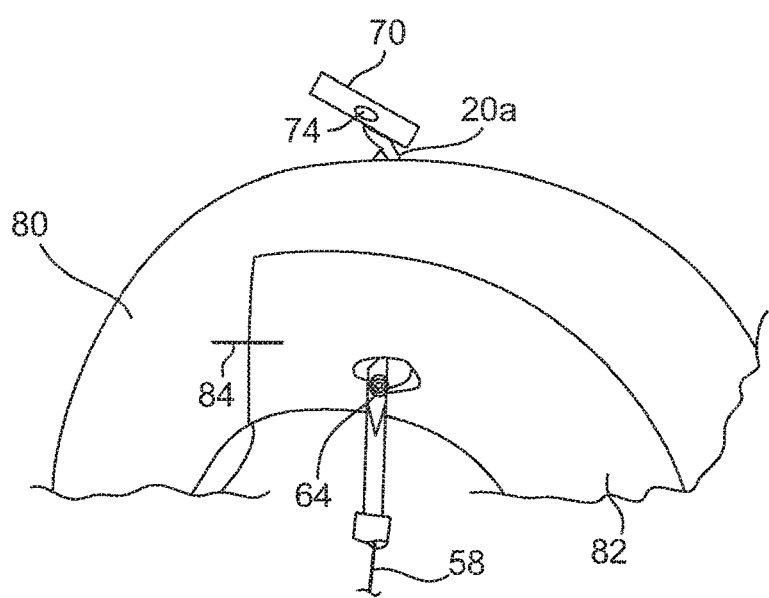
FIG. 33 is a top view of the needle of FIG. 32 after the first anchor has been ejected from the needle with the pusher.

While griping the handle 16 and the trigger 30 on the applicator 10, the user inserts the needle 20*a* into a patient at an incision site so that the needle 20*a* may then be inserted through the implant 82 and through the meniscus 80 at a first location 86, preferably near the center of the implant 82, to a side opposite the insertion site, as shown in FIG. 32. The user should be sure that the hitch knot 74 on the anchor 70 has passed through the meniscus 80, as shown in FIG. 32. In an embodiment, the user then advances the pusher 23 via the trigger 30 until the anchor 70 is pushed outside the needle 20*a*, as shown in FIG. 33. The user should be careful to not advance the pusher 23 further to avoid the premature deployment of the anchor 60. The use of the spacer 28 assists in preventing the premature deployment of the anchor 60. In addition to, or in lieu of the spacer 23, the dimple 39*a* that is located near the point 38*a* of the needle 20*a* may also be used to provide the user with tactile feedback that the anchor 60 has been advanced to its proper pre-deployment position.

Figure 34:
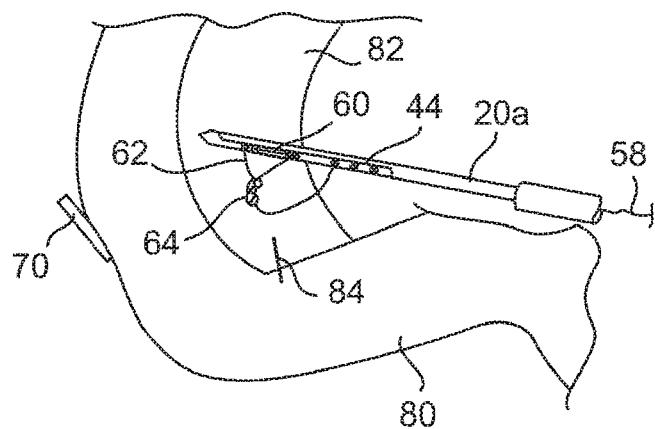
FIG. 34 is a perspective view of the needle of FIG. 32 after it has been pulled back through the meniscus and implant.

As shown in FIG. 34, the user then retracts the needle 20*a* slowly from the meniscus 80 and the implant 82, leaving the anchor 70 behind on the opposite side of the meniscus 80. The anchor 60 will remain inside the needle 20*a*. If the user hasn't already done so, the user next advances the anchor 60 until the anchor 60 is located near the point 38*a* of the needle 20*a*. Again for embodiments that include the dimple 39*a*, the dimple 39*a* may be used to guide the user to correctly position the anchor 60.

Figure 35:
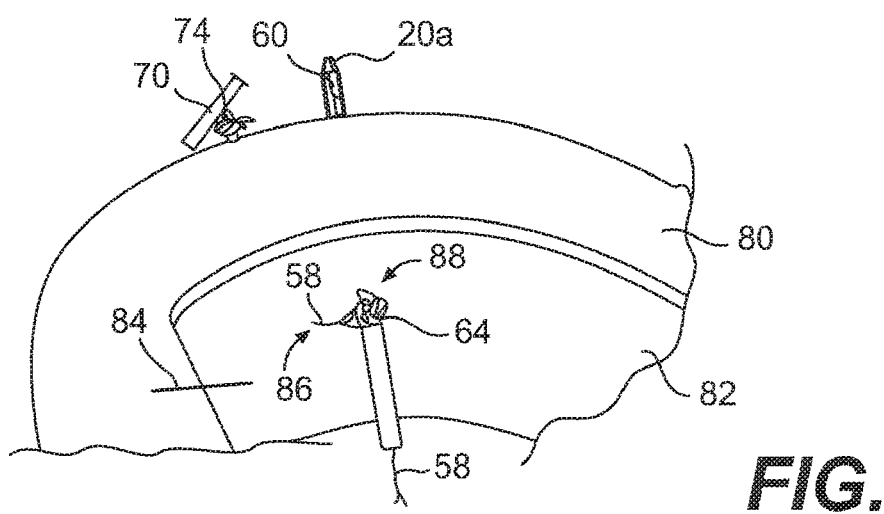
FIG. 35 is a top view of the needle of FIG. 32 piercing the implant and meniscus of FIG. 25 at a second location.
Figure 36:
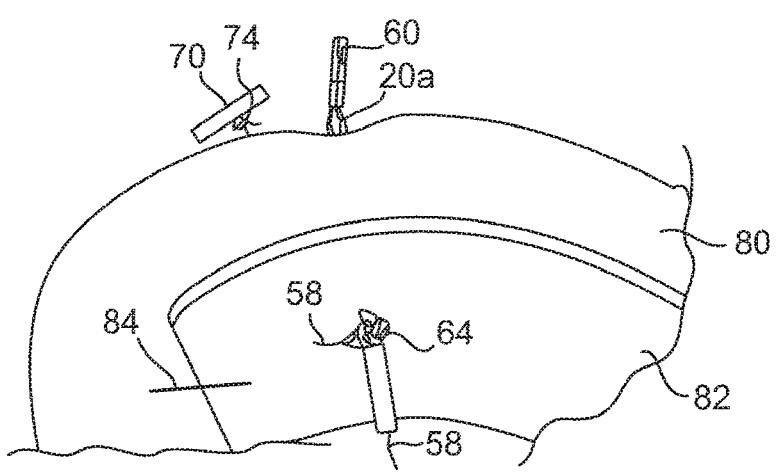
FIG. 36 is a top view of the needle of FIG. 35 after the second anchor has been ejected from the needle with the pusher.
Figure 37:
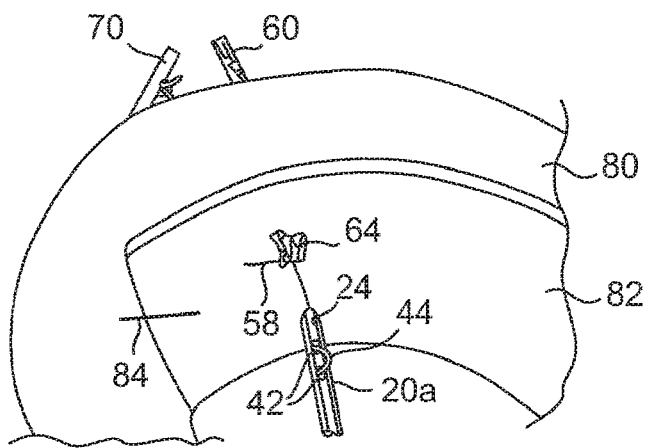
FIG. 37 is a top view of the needle of FIG. 35 after is has been pulled back through the meniscus and implant.

While gripping the handle 16 and the trigger 30 on the applicator 10, the user inserts the needle 20a though the implant 82 and through the meniscus 80 at a second location 88, which is preferably near the first location 86, until the center of the anchor 60 is outside the opposite side of the meniscus 80, as shown in FIG. 35. If the user hasn't already done so, the user next removes the spacer 28 from the rod 24 by grasping the tab 29 and pulling the spacer 28 away from the rod 24. The user then advances the pusher 3 until the anchor 60 is pushed outside the needle 20a, as shown in FIG. 36. The user then retracts the needle 20a, thereby leaving the anchor 60 on the opposite side of the meniscus 80, as shown in FIG. 37.

Figure 38:
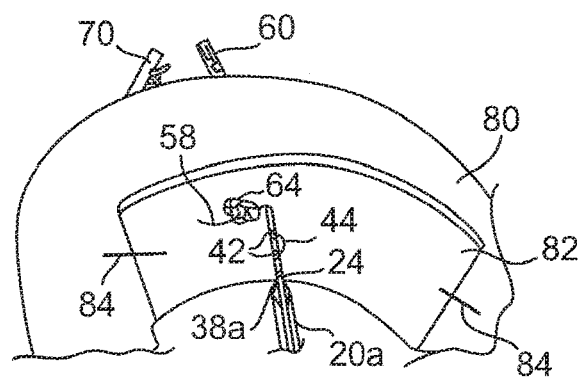
FIG. 38 is a top view of the needle of FIG. 37 with the pusher extended out of the needle.
Figure 39:
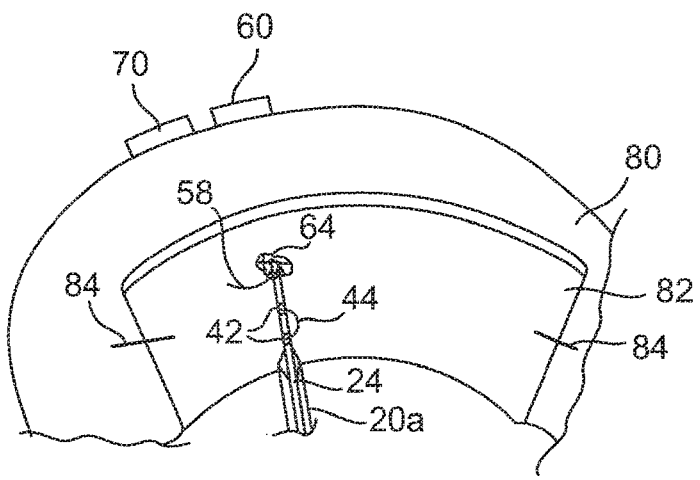
FIG. 39 is a top view of the needle of FIG. 38 with the pusher pushing the knot against the implant.
Figure 40:
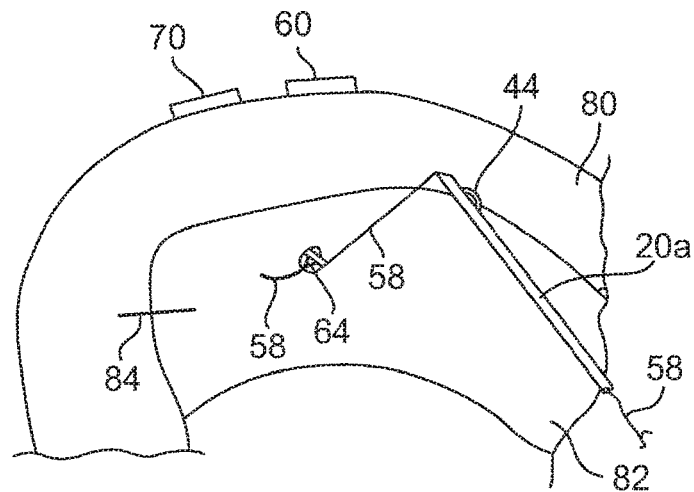
FIG. 40 is a top view of the needle of FIG. 39 after it has been pulled back following knot pushing and suture tensioning.

Having deployed both anchors 60, 70, the user may then advance the pusher 23 via the trigger 30 so that the rod 24 extends approximately 1 cm beyond the point 38a of the needle 20a, as shown in FIG. 38. While gripping the handle 16 and the trigger 30 of the applicator 10, the user then holds the tip of the rod 24 against the knot 64 and pushes the knot 64 to the surface of the implant 82, being careful not to push the knot 64 through the implant 82. The user continues to grip the handle 16 and the trigger 30 while gently pulling on the end 59 of the flexible portion 58 of the suture 12 at the proximal end 15 of the body portion 14 of the applicator 10 until slack in the suture 12 is taken up, and the anchors 60, 70 sit flat against the meniscus 80, as shown in FIGS. 39 and 40.

Figure 41:
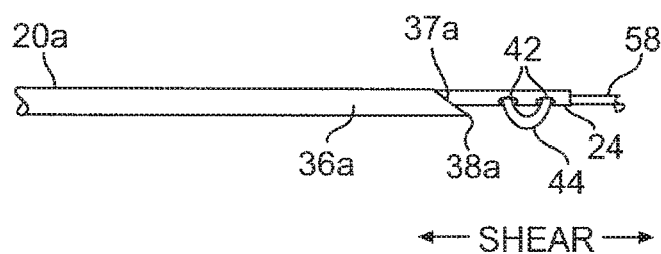
FIG. 41 is a side view of the needle of FIG. 40 with the suture exposed to the needle cutting surface.
Figure 43:
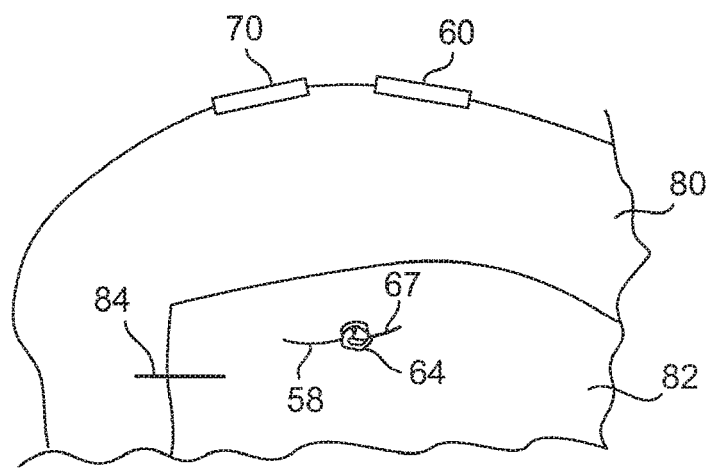
FIG. 43 is a top view of the repaired meniscus with the suture tightly in place.

With the knot 64 now secured, the user may extend the rod 24 of the pusher 23 out of the needle 20a approximately 1 cm. The user may then rotate the pusher 23 up to approximately 180°, or until the slots 42 and the exposed portion 44 of the suture 12 are positioned to come into contact with the cutting surface 37a when the pusher 23 is pulled back toward the proximal end 15 of the body portion 14 of the applicator 10, as shown in FIG. 41. Holding the end 59 of the flexible portion 58 that extends out of the proximal end 15, the user may shear the exposed portion 44 of the suture 12 against the cutting surface 37a by sliding the pusher 23 longitudinally against the cutting surface 37a, as shown in FIG. 41, thereby leaving a short tail 67 near the knot 64, as shown in FIG. 43. The pusher 23 may have to be moved back and forth against the cutting surface 37a before the suture 12 is fully cut.

Figure 42:
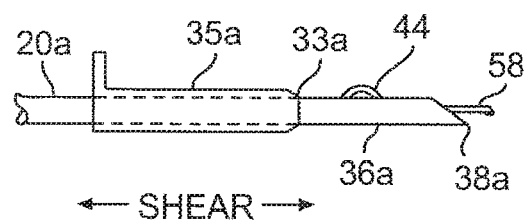
FIG. 42 is a side view of another embodiment of the needle of FIG. 40 with the suture exposed to a cutting surface on a cutting sheath.

In another embodiment, after the knot 64 is secured, while holding the end 59 of the flexible portion 58 that extends out of the proximal end 15, the user may shear the exposed portion 44 of the suture 12 against the cutting surface 33a by sliding the cutting sheath 35a along the distal end 36a and toward the point 38a of the needle 20a, as shown in FIG. 42, thereby leaving a short tail 67 near the knot 64, as shown in FIG. 43. The cutting sheath 35a may have to be moved back and forth along the distal end of the needle 20a before the suture 12 is fully cut.

The aforementioned system 1 and method provide au all-inside suture fixation to the implant and meniscus, because the needle 20a of the applicator 10 has not been removed from the patient's body between the deployment of the anchor 70, the pushing of the knot 64, and the cutting of the excess flexible portion 58 of the suture 12. This may be beneficial to the patient because it may reduce the time the applicator 10 is in the patient's body, and allows for a single, small entry point of the needle 20a, at the incision, into the patient's body.

The user may then repeat the steps shown in FIGS. 32-43 for any remaining sutures 12 that are needed to complete the fixation of the implant 82 to the meniscus 80. Generally, it may take three or more sutures 12 to secure the implant 82.

Of course, in alternative embodiments, the user may remove the body portion 14 of the applicator 10 and pusher 23 from the cannula 18, and trim the excess flexible portion 58 of the suture 12 with scissors, or some other cutting device. The illustrated embodiments are not intended to be limiting in any way.

Also, in alternative embodiments, one or both of the anchors 60, 70 may be the anchor described above that includes one or more barbs. This allows the user to advance the pusher 23 via the trigger 30 only until a distal end of the anchor is located adjacent the point of the needle 20 in an orientation in which the barb is no longer engaged by the wall of the needle 20. When the anchor is in this position, the wall of the needle 20 is no longer exerting pressure on the barb, thereby allowing the barb to be biased outward and away from the body of the anchor. The barb may then be used to engage the anchor with the meniscus 80 so that when the user pulls the needle 20 back through the meniscus 80 and the implant 82, the entirety of the anchor will pull out of the needle 20 without further advancement of the pusher 23.

It is also contemplated that the needle 20 may be designed such that the tab 48 on the anchor 46 may be used to engage the anchor 46 with the meniscus 80 before the anchor 46 exits the needle 20. This allows the entirety of the anchor 46 to be pulled out of the needle 20 when the needle 20 is pulled back through the meniscus 80, rather than pushing the entirety of the anchor 46 out of the needle 20 with the pusher 23, as described in the embodiments above.

Although the above-described procedure was in the context of attaching an implant to a meniscus with needle penetration of the implant and the meniscus in a substantially horizontal stitch, a substantially similar procedure may be used for the placement of other types of stitches, such as vertical and oblique, as would be appreciated by one of skill in the art. The illustrated and described embodiments should not be considered to be limiting in any way.

In addition, although the above-described procedure was in the context of attaching an implant to a meniscus, a substantially similar procedure may be used to repair soft tissue, as would be appreciated by one of skill in the art. The illustrated and described embodiments should not be considered to be limiting y way. For example, to repair a tear in the meniscus 80 with the suture 12, the needle 20 may be inserted through the meniscus 80 a first location near the tear. The first anchor 70 of the suture 12 may then be delivered to an opposite side of the meniscus 80, and the needle 20 retracted from the meniscus 80, without pulling out of the body. The needle may then be inserted through the meniscus 80 at a second location on an opposite side of the tear as the first location. The second anchor 60 of the suture 12 may then be delivered to the opposite side of the meniscus 80. Once the second anchor 60 is in the proper position, the user may then push the knot 64 to a surface of the meniscus 80 to tighten the suture. The excess of the flexible portion 58 of the suture 12 may then be cut with any of the cutting methods described above.

In another embodiment, illustrated in FIGS. 44-52C, a system 100 for repairing a meniscus is provided. The system 100 includes an applicator 110 that is constructed and arranged to deploy the suture 12, which includes the flexible portion 58 and the two anchors 60, 70, as described above, to the meniscus. In this embodiment, the applicator 110 includes a body portion 114 that is configured to be grasped by the user. As shown in FIGS. 44 and 45, the body portion 114 includes a pair of extensions 116 at a proximal end 115 of the body portion 114. Each of the extensions 116 is constructed and arranged to engage a finger of the user such that the body portion 114 is may be held in between the fingers in a similar way that a syringe is typically held.

As illustrated in FIG. 44, the body portion 114 of the applicator 110 receives a cannula 118 that extends from a distal end 113 of the body portion 114 in a direction that is away from the proximal end 115. The cannula 118 may be constructed and arranged like the cannula 18 described and illustrated above, and in U.S. Pat. No. 5,928,252, which is hereby incorporated by reference in its entirety, and may be connected to the body portion 114 in a similar manner.

The applicator 110 also includes a needle 120 that has a cutting surface 121 at a distal end thereof. The needle 120 is connected to a distal end of the cannula 118 so that it is operatively connected to the distal end 113 of the body portion 114. Of course, the needle 120 may be considered to be a part of the cannula 118 itself. The needle 120 may be of the same design as the needle 20*a* discussed above. As such, details of the needle 120 will not will be described in further detail. Instead, reference should be made to the needle previously described and illustrated.

The applicator 110 also includes a pusher 123. The pusher 123 includes a rod 124 (shown in FIG. 46) that extends through a central lumen 112 of the body portion 114, a central bore (not shown) of the cannula 118, and is slidingly received by the needle 120. A knob 126 is attached to one end of the rod 124 and is configured to be grasped by the user so that the user may manipulate the rod 124, as described in further detail below. As shown in FIG. 46, the rod 124 includes proximal end 125 and a distal end 127, which has a smaller diameter than the diameter of proximal end 125, as illustrated. The distal end 127 is configured to include a pair of slots 142 that are similar to the slots 42 discussed above. A central bore 122 extends through the rod 124 and the knob 126 so that the flexible portion 58 of the suture 12 may be threaded through the slots 142, through the rod 124, and through the knob 126, as Shown in FIG. 46.

As illustrated in FIG. 46, the pusher 123 includes a first projection 128 that projects from the rod 124 and defines a first stop surface 129 on one side thereof. The first projection 128 may be configured as a square or rectangular tab, or may be in the shape of a cylinder. The illustrated embodiment is not intended to be limiting in any way. The knob 126 of the pusher 123 includes a stopper portion 130 that is connected to the rod 124 and defines a second stop surface 131. The pusher 123 also includes a second projection 132 that projects from the rod 124 and defines a third stop surface 133 on one side thereof. The second projection 130 is axially spaced from the first projection 128 and is axially located between the first projection 128 and the distal end 127 of the rod 124.

As shown in FIG. 47, the second projection 130 is also radially spaced from the first projection 128. The radially spacing is defined by angle β, and in the illustrated embodiment, the angle β is about 90°. It is contemplated that the angle β may be in the range of about 10° to about 370°, as will be appreciated in the discussion below. The illustrated embodiment is not intended to be limiting in any way.

As shown in FIG. 45, the body portion 114 defines an outer surface 134 at its proximal end that is configured to engage the stop surfaces 129, 131, 133 described above as the pusher 123 is moved to different positions relative to the body portion 114 and needle 120. The body portion 114 also includes an opening 36, shown in the Figures to be shaped as a keyhole, that is axially connected to the central lumen 112 and is constructed and arranged to receive the first projection 128 and the second projection 130 of the pusher 123, as discussed in further detail below. The arrangement of the opening 136 in the proximal end 115 of the body portion 114 is such that the pusher 123 should be in the proper orientation relative to the body portion 114 in order for the pusher 123 to move toward the needle 120 in an axial direction. Once the first projection 128 or the second projection 130 has passed through the opening, the respective projection 128, 130 is then located within the central lumen 112 of the body portion 114. The central lumen 112 is sized to allow the projections 128, 130 to rotate with the rod 124 about a central axis. However, when one of the projections 128, 130 is positioned within the opening 136, the rod 124 will be prevented from rotating.

FIGS. 48A-53C illustrate portions of the system 100 during different stages of repairing a meniscus or other soft tissue. As shown in FIGS. 48A-C, the pusher 123 is disposed in a first orientation and first axial position relative to the body portion 114 and the needle 120. In this orientation and position, the third stop surface 133 is engaged with the outer surface 134 of the body portion 114 such that pressure applied to the knob 126 toward the body portion 114 will not cause the pusher 123 to move in an axial direction. This allows the first anchor 70 to stay within the needle 120, as shown in FIG. 48C, even if pressure is applied to the pusher 123 via the knob 126. This may allow the user to apply pressure to the applicator 110 via the knob 126 as the needle 120 is initially inserted through the implant 82 and meniscus 80, as described above. For example, the user may hold the body portion 114 and engage the extensions 116 with two fingers, while applying pressure to the knob 126 with a thumb, like a syringe.

Once the needle 120 is in the proper location for the discharge of the first anchor 70, the user may rotate the pusher 123, via the knob 126, to a second orientation, which is 90° from the first orientation, as shown in FIGS. 49A-C. This orientation aligns the second projection 132 of the pusher 123 with the opening 136 of the body portion 114, as shown in FIG. 49B. Because the pusher 123 has not yet been moved axially, the first anchor 70 is still located in the needle 120, as shown in FIG. 49C.

The user may then apply pressure to the pusher 123 in an axial direction via the knob 126 until the first surface 129 of the first projection 128 engages the outer surface 134 of the body portion 114, as shown in FIG. 50A. At this position, the second projection 132 has passed all the way through the opening 136 of the body portion 114 such that is in the central lumen 112. As shown in FIG. 50C, the first anchor 70 has been discharged by the pusher 123 out of the needle 120. Other aspects of the discharge of the anchor 70 are discussed above and shown in FIG. 33.

As discussed above and shown in FIGS. 34 and 35 with reference to the needle 20*a*, the user may then pull the needle 120 in a similar manner so that it clears the meniscus 80 and the implant 82, and then insert the needle through the implant 82 and the meniscus 80 at a second location. Once the distal end of the needle 120 is in the location where the second anchor 60 should be discharged, the user may then rotate the pusher 123 to a third orientation, as shown in FIGS. 51A-C, which is 90° from the second orientation, and 180° from the first orientation. At this orientation, the first protrusion 128 is aligned with the opening 136, and the second anchor 60 is still located within the needle 120.

The user may then apply pressure to the pusher 123 via the knob 123 until the second stop surface 131 of the stopper 130 engages the outer surface 134 of the body portion 114, as shown in FIGS. 52A-B. As illustrated, in this position, the first projection 128 has passed all of the way through the opening 136 and is in the central lumen 112 of the body portion 114. As shown in FIG. 52C, the second anchor 60 has been discharged from the needle 120 by the pusher 123. Other aspects of the discharge of the second anchor 60 are discussed above and shown in FIG. 36. As discussed above and shown in FIGS. 37-40, the knot 64 of the suture 12 may then be pushed against the implant 82, although in this embodiment, the distal end 127 of the rod 124 of the pusher 123 is used to push the knot 64 rather than the rod 24 shown in FIGS. 37-40. Once the knot 64 has been tightened and any slack is taken out of the flexible portion 58 of the suture 12, the pusher 123 may be rotated out of the third orientation, as shown in FIGS. 52A-C so as to shear the flexible portion 58 of the suture 12 against the cutting surface 121 of the needle 120. Once the flexible portion 58 has been cut, the applicator 110 may be pulled out of the body. The applicator 110 may then be disposed of, or, if desired, may be cleaned, sterilized, and used again.

The foregoing disclosure of embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. For example, any number of sutures may be prepared ahead of time. In addition, the advancement of the anchors within the cannula may occur before or after needle insertion. In addition, the delivery of the second anchor may not require that the needle be fully withdrawn; for example when two anchors are to be delivered through a single insertion site. As one of ordinary skill in the art would appreciate, other sequences of steps may be possible. Therefore, the particular order of the steps set forth herein should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A medical instrument, comprising:
a body portion having a proximal handle portion including an opening, a distal cannula extending from the handle portion, the distal cannula extending distally to a tip having a cutting surface, and a lumen extending through the handle portion and distal cannula; and
a pushrod positioned through the lumen and is slidingly received by the tip of the distal cannula, the pushrod including a first stop projection and a second stop projection positioned along a length of the pushrod, the first and second projections being distal to a proximal handle portion of the pushrod, the tip of the distal cannula providing a tactile feedback when the pushrod is pushed to a first location;
wherein, the pushrod can travel in a first distal direction towards the first location to the first stop projection which prevents further distal movement of the pushrod, wherein an anchor is positioned within the cannula distal to the pushrod, such that with the pushrod in a first position, the anchor remains within the cannula proximal to the first location, and with the pushrod in the second position, the distal movement of the pushrod moves the anchor distal to the first location and expels the anchor from the tip of the distal cannula.

2. The instrument of claim 1, wherein the proximal handle portion of the body portion includes at least one extension for engagement by a user.

3. The instrument of claim 1, wherein the distal movement of the pushrod through the body portion is defined to a predetermined distance.

4. The instrument of claim 1, wherein the distal cannula further comprises a dimple positioned within the lumen of the distal cannula.

5. The implant of claim 4, wherein the dimple is positioned at the first location and provides a user with the tactile feedback as to the position of the anchor.

6. A medical instrument, comprising:
a body portion having a proximal handle portion, a distal cannula extending from the handle portion, the distal cannula extending distally to a tip having a cutting surface, and a lumen extending through the handle portion and distal cannula;
a pushrod positioned through the lumen and is slidingly received by the tip of the distal cannula, the tip of the distal cannula providing a tactile feedback when the pushrod is pushed to a first location; and
a first stop formed between a first stop projection of the pushrod and a surface of the body portion and a second stop formed between a second stop projection of the pushrod and a surface of the body portion, wherein upon moving the pushrod from a first position to the first location and to a second position to expel a first anchor, the first stop prevents distal movement of the pushrod relative to the body portion beyond the second position, and with the pushrod in a third position, the pushrod can move distally relative to the body portion to a fourth position to expel a second anchor, the second stop prevents distal movement of the pushrod relative to the body portion beyond the fourth position, the first and second stop projections of the pushrod being distal to a proximal handle portion of the pushrod,
wherein the first anchor is positioned within the cannula distal to the pushrod, such that with the pushrod in the first position, the anchor remains within the cannula proximal to the first location, and with the pushrod in the second position, the distal movement of the pushrod moves the first anchor distal to the first location and expels the anchor from the tip of the distal cannula.

7. The instrument of claim 6, wherein a third stop is spaced axially from the second stop, and the second stop is spaced axially from the first stop such that, at each successive stop, the pushrod is positioned more distally within the lumen.

8. The instrument of claim 6, wherein the pushrod is rotatable relative to the body portion.

9. The instrument of claim 6, wherein the distal cannula further comprises a dimple positioned within the lumen of the distal cannula.

10. The instrument of claim 9, wherein the dimple is positioned at the first location and provides a user with the tactile feedback as to the position of the anchor.

11. A medical instrument, comprising:
a body portion having a proximal handle portion including an opening, a distal cannula extending from the handle portion, the distal cannula extending distally to a tip having a cutting surface, and a lumen extending through the handle portion and distal cannula; and a pushrod positioned through the lumen and is slidingly received by the tip of the distal cannula, the pushrod including a first stop surface positioned along the length of the pushrod, the tip of the distal cannula providing a tactile feedback when the distal end of the pushrod is pushed to a first location;

wherein, in a first position of the first stop surface, the first stop surface can pass freely through the body portion to allow distal movement of the first stop surface through the body portion, and in a second position, the first stop surface is in contact with the body portion to prevent distal movement of the first stop surface through the body portion, the first stop surface having a third position, corresponding with the first location of the distal end of the pushrod, in between the first position and the second position, the first stop surface of the pushrod being distal to a proximal handle portion of the pushrod, wherein an anchor is positioned within the cannula distal to the pushrod, such that with the pushrod in the first position, the anchor remains within the cannula proximal to the first location, and with the pushrod in the second position, the distal movement of the pushrod moves the anchor distal to the first location and expels the anchor from the tip of the distal cannula.

12. The instrument of claim 11, wherein the proximal handle portion of the body portion includes at least one extension for engagement by a user.

13. The instrument of claim 11, wherein the distal movement of the pushrod through the body portion is defined to a predetermined distance.

14. The instrument of claim 11, wherein the distal cannula further comprises a dimple positioned within the lumen of the distal cannula.

15. The implant of claim 14, wherein the dimple is positioned at the first location and provides a user with the tactile feedback as to the position of the anchor.

* * * * *